(12) United States Patent
Mueller et al.

(10) Patent No.: US 11,701,037 B2
(45) Date of Patent: Jul. 18, 2023

(54) METHOD AND ELECTRONICS UNIT FOR DETECTING IN-VIVO PROPERTIES OF A BIOSENSOR

(71) Applicant: Roche Diabetes Care, Inc., Indianapolis, IN (US)

(72) Inventors: Ulrich Mueller, Mannheim (DE); Herbert Wieder, Mannheim (DE); Alexander Poggenwisch, Mannheim (DE); Uli Delventhal, Mannheim (DE); Andreas Knoerzer, Stuttgart (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 531 days.

(21) Appl. No.: 16/723,390

(22) Filed: Dec. 20, 2019

(65) Prior Publication Data

US 2020/0178868 A1 Jun. 11, 2020

Related U.S. Application Data

(63) Continuation of application No. PCT/EP2018/067619, filed on Jun. 29, 2018.

(51) Int. Cl.
*A61B 5/1486* (2006.01)
*A61B 5/1495* (2006.01)
*A61B 5/145* (2006.01)

(52) U.S. Cl.
CPC ...... *A61B 5/14865* (2013.01); *A61B 5/14532* (2013.01); *A61B 5/1495* (2013.01); *A61B 2560/0228* (2013.01)

(58) Field of Classification Search
CPC ............ A61B 5/14865; A61B 5/14532; A61B 2560/0228; A61B 2560/0223; A61B 2562/0209; A61B 5/1486; A61B 5/1491

(Continued)

(56) References Cited

U.S. PATENT DOCUMENTS

| 5,413,690 A | 5/1995 | Kost et al. |
| 5,762,770 A | 6/1998 | Pritchard et al. |

(Continued)

FOREIGN PATENT DOCUMENTS

| CN | 101105471 A | 1/2008 |
| CN | 106061370 A | 10/2016 |

(Continued)

OTHER PUBLICATIONS

International Preliminary Report on Patentability, PCT/EP2018/067619, dated Sep. 12, 2019, 13 pages.

(Continued)

*Primary Examiner* — Navin Natnithithadha
(74) *Attorney, Agent, or Firm* — Bose McKinney & Evans LLP

(57) ABSTRACT

A method for detecting in-vivo properties of a biosensor. In the inventive method, a sensitivity-to-admittance relation is provided and a raw current in the biosensor is measured. An in-vivo current response is also measured at first and second operating points. A time constant $\tau$ is determined by the electrical capacitance C of the working electrode and the electrical resistance $R_M$ of the membrane by $\tau = R_M \cdot C$. The first and second operating points are selected below and above $\tau$, respectively. An analyte value in a sample of a body fluid is determined by using the raw current and compensating sensitivity drift in the biosensor, which in turn is compensated by using the measured value for the raw current and a corrected value for the sensitivity. The failsafe operation of the biosensor is monitored by using the in-vivo current response measured at the first and second operating points.

13 Claims, 11 Drawing Sheets

(58) Field of Classification Search
USPC .......................................... 600/309, 345–366
See application file for complete search history.

(56) References Cited

U.S. PATENT DOCUMENTS

| | | | |
|---|---|---|---|
| 5,798,031 A | 8/1998 | Charlton et al. | |
| 6,129,823 A | 10/2000 | Hughes et al. | |
| 6,360,888 B1 | 3/2002 | McIvor et al. | |
| 9,149,220 B2* | 10/2015 | Bohm | A61B 5/1486 |
| 10,004,442 B2* | 6/2018 | Böhm | G01N 27/026 |
| 10,327,688 B2* | 6/2019 | Böhm | A61B 5/1495 |
| 10,555,695 B2* | 2/2020 | Böhm | H05K 999/00 |
| 10,561,354 B2* | 2/2020 | Böhm | G01D 18/00 |
| 10,610,141 B2* | 4/2020 | Böhm | A61B 5/14517 |
| 10,624,568 B2* | 4/2020 | Böhm | G01N 33/49 |
| 10,682,084 B2* | 6/2020 | Böhm | A61B 5/14517 |
| 10,722,162 B2* | 7/2020 | Böhm | G01D 18/00 |
| 10,835,162 B2* | 11/2020 | Böhm | A61B 5/1451 |
| 10,980,461 B2* | 4/2021 | Simpson | A61B 5/1495 |
| 2005/0013731 A1 | 1/2005 | Burke et al. | |
| 2007/0299617 A1 | 12/2007 | Willis | |
| 2008/0105568 A1 | 5/2008 | Wu | |
| 2008/0242962 A1 | 10/2008 | Roesicke et al. | |
| 2010/0169035 A1 | 7/2010 | Liang et al. | |
| 2011/0297557 A1 | 12/2011 | Wu et al. | |
| 2012/0262298 A1 | 10/2012 | Bohm et al. | |
| 2013/0245401 A1 | 9/2013 | Estes et al. | |
| 2015/0001070 A1 | 1/2015 | Mackintosh | |
| 2015/0164371 A1 | 6/2015 | Varsavsky et al. | |
| 2015/0164387 A1* | 6/2015 | Varsavsky | A61B 5/1495 702/182 |
| 2016/0041117 A1 | 2/2016 | Buck, Jr. et al. | |
| 2016/0091450 A1 | 3/2016 | McColl et al. | |
| 2016/0296148 A1 | 10/2016 | Hayter et al. | |
| 2019/0133506 A1* | 5/2019 | Ringemann | A61B 5/14865 |

FOREIGN PATENT DOCUMENTS

| | | |
|---|---|---|
| CN | 107003270 A | 8/2017 |
| JP | 2014-514093 A | 6/2014 |
| JP | 2016-510120 A | 4/2016 |
| JP | 2016-523369 A | 8/2016 |
| RU | 2 386 960 C2 | 4/2010 |
| RU | 2 566 382 C2 | 10/2015 |

OTHER PUBLICATIONS

International Search Report and Written Opinion of the International Searching Authority, PCT/EP2018/067619, dated Sep. 18, 2018, 17 pages.

European Search Report, EP 17 179 366.4, dated Dec. 15, 2017, 12 pages.

* cited by examiner

METHOD AND ELECTRONICS UNIT FOR DETECTING IN-VIVO PROPERTIES OF A BIOSENSOR

RELATED APPLICATIONS

This application is a continuation of PCT/EP2018/067619, filed Jun. 29, 2018, which claims priority to EP 17 179 366.4, filed Jul. 3, 2017, the entire disclosures of each of which are hereby incorporated herein by reference.

BACKGROUND

This disclosure relates to a method for detecting in-vivo properties of a biosensor, to an electronics unit adapted for performing this method, and to a system comprising a biosensor and such a kind of electronics unit. The method, the electronics unit and the system according to this disclosure may, primarily, be used for a long-term monitoring of an analyte concentration in a body fluid, in particular for a long-term monitoring of a glucose level or of the concentration of one or more other types of analytes in a body fluid. This disclosure may both be applied in the field of home care as well as in the field of professional care, such as in hospitals. However, other applications are feasible.

Monitoring certain body functions, more particularly monitoring one or more concentrations of certain analytes, plays an important role in the prevention and treatment of various diseases. Without restricting further possible applications, this disclosure is described in the following with reference to glucose monitoring in an interstitial fluid. However, this disclosure can also be applied to other types of analytes. Blood glucose monitoring may, specifically, be performed by using electrochemical biosensors besides optical measurements. Examples of electrochemical biosensors for measuring glucose, specifically in blood or other body fluids, are known from U.S. Pat. Nos. 5,413,690 A, 5,762,770 A, 5,798,031 A, 6,129,823 A or U.S. Publication No. 2005/0013731 A1.

In addition to "spot measurements" in which a sample of a body fluid is taken from a user, i.e., a human or an animal, in a targeted fashion and examined with respect to the analyte concentration, continuous measurements have become increasingly established. Thus, in the recent past, continuous measuring of glucose in the interstitial tissue, also referred to as "continuous glucose monitoring" or abbreviated to "CGM," has been established as another important method for managing, monitoring, and controlling a diabetes state. Herein, an active sensor region is applied directly to a measurement site which is, generally, arranged in an interstitial tissue, and may, for example, convert glucose into an amended entity by using an enzyme, in particular, glucose oxidase, generally abbreviated to "GOD." As a result, the detectable current may be related to the glucose concentration and can, thus, be used as a measurement variable. Examples of such transcutaneous measurement systems are described in U.S. Pat. No. 6,360,888 B1 or U.S. Publication No. 2008/0242962 A1.

U.S. Publication No. 2012/262298 A1 discloses methods and devices for processing sensor data and self-calibration. Herein, methods and devices are provided which are capable of calibrating a continuous analyte sensor based on an initial sensitivity, and then continuously performing self-calibration without using, or with reduced use of, reference measurements. Also described herein are methods and devices for determining a property of an analyte sensor using a stimulus signal, wherein the property of the sensor can be used to compensate sensor data for sensitivity drift, or determine another property associated with the sensor, such as temperature, sensor membrane damage, moisture ingress in sensor electronics, and scaling factors.

Typically, current continuous monitoring systems are transcutaneous systems or subcutaneous systems. Accordingly, the actual biosensor or at least a measuring portion of the biosensor may be arranged under the skin of the user. However, an evaluation and control part of the system, which may also be referred to as a "patch," may, generally, be located outside of the body of a user. Herein, the biosensor is generally applied by using an insertion instrument, which is, in an exemplary fashion, described in U.S. Pat. No. 6,360,888 B1. However, other types of insertion instruments are also known. Further, a control part may, typically, be required which may be located outside the body tissue and which has to be in communication with the biosensor. Generally, communication is established by providing at least one electrical contact between the biosensor and the control part, wherein the contact may be a permanent electrical contact or a releasable electrical contact. Other techniques for providing electrical contacts, such as by appropriate spring contacts, are generally known and may also be applied.

In continuous glucose measuring systems, the concentration of the analyte glucose may be determined by employing an electrochemical sensor comprising an electrochemical cell having at least a working electrode and a counter electrode. Herein, the working electrode may have a reagent layer comprising an enzyme with a redox active enzyme co-factor adapted to support an oxidation of the analyte in the body fluid.

SUMMARY

This disclosure provides a method for detecting in-vivo properties of a biosensor, an electronics unit adapted for performing this method, and a system comprising a biosensor and such an electronics unit, which at least partially avoid the shortcomings of known devices and methods of this kind.

In particular, the method taught herein is capable of detecting a possible in-vivo drift in the biosensor in a reliable and recurrent manner, wherein an actually detected in-vivo drift may, subsequently, be applicable for compensating the effects of the drift in biosensor, particularly in order to be capable of determining an analyte value reliably and recurrently.

Further, the method according to this disclosure may easily be implemented in an electronics unit which may be operable with standard biosensors and may, thus, be applicable in existing biosensor systems without essential amendments.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. Further, it shall be understood for purposes of this disclosure and appended claims that, regardless of whether the phrases "one or more" or "at least one" precede an element or feature, such element or feature should be interpreted to mean "at least one" or "one or more," unless it is made explicit herein that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. This disclosure may, as the skilled person will recognize, be performed by using alternative features. Similarly, features introduced by "in an embodiment of this disclosure" or similar expressions are intended to be optional features, without any restriction regarding alternative embodiments of this disclosure, without any restrictions regarding the scope of this disclosure and without any restriction regarding the possibility of combining the features introduced in such way with other optional or non-optional features of this disclosure.

In a first aspect, a method for detecting in-vivo properties of a biosensor is disclosed, wherein the biosensor is, in interoperation with an electronics unit, adapted for electrochemically determining at least one value of an analyte in a sample of a body fluid, wherein the biosensor comprises at least one working electrode, wherein the working electrode is covered by a membrane and includes an enzyme for providing a reaction with the analyte, wherein the membrane has an electrical resistance and the working electrode has an electrical capacitance, wherein the electronics unit is adapted for measuring a raw current and a current response indicative of an admittance of the biosensor. Herein, the method comprises the following method steps which are listed as follows:

a) providing a sensitivity-to-admittance relation of the biosensor;
  b) measuring a raw current in the biosensor;
  c) measuring an in-vivo current response indicative of the in-vivo admittance of the biosensor, wherein the in-vivo current response is measured at at least one first operating point and at at least one second operating point, wherein the first operating point is selected for providing a first characteristic value being related to the electrical resistance of the membrane, and wherein the second operating point is selected for providing a second characteristic value being related to the electrical capacitance of the working electrode; and
  d) determining an analyte value in a sample of a body fluid by using the raw current and compensating an in-vivo sensitivity drift in the biosensor by correcting the measured value for the raw current by determining an actual value of the sensitivity by using the first characteristic value, whereby the sensitivity-to-admittance relation as provided during step a) is taken into account; and
  e) monitoring a failsafe operation of the sensor based on the first characteristic value and/or the second characteristic value.

Herein, the indicated steps may, preferably, be performed in the given order, thereby commencing with method step a) and finishing with method step d), wherein, however, any or all of the indicated steps, in particular method steps b) and c), may be performed at least partially concurrently, such as over a definite period of time. Additionally, any or all of the indicated steps may also be repeated several times in order to allow for detecting in-vivo properties of the biosensor, such as after a prespecified time or as a consequence of an occurrence of a prespecified event. Further, additional method steps, whether described herein or not, may be performed, too.

As generally used, the term "biosensor" may refer to an arbitrary device being configured for conducting at least one medical analysis. For this purpose, the biosensor may be an arbitrary device configured for performing at least one diagnostic purpose and, specifically, comprising at least one analyte sensor for performing the at least one medical analysis. The biosensor may, specifically, comprise an assembly of two or more components capable of interacting with each other, such as in order to perform one or more diagnostic purposes, such as in order to perform the medical analysis. Specifically, the two or more components may be capable of performing at least one detection of the at least one analyte in the body fluid and/or in order to contribute to the at least one detection of the at least one analyte in the body fluid. Generally, the biosensor may also be part of at least one of a sensor assembly, a sensor system, a sensor kit or a sensor device. Further, the biosensor may be connectable to an evaluation device, such as to an electronics unit.

In a preferred embodiment, the biosensor may be a fully or a partially implantable biosensor which may, particularly, be adapted for performing the detection of the analyte in the body fluid in a subcutaneous tissue, in particular, in an interstitial fluid. As used herein, the terms "implantable biosensor" or "subcutaneous biosensor" may refer to an arbitrary biosensor being adapted to be fully or at least partly arranged within the body tissue of the patient or the user. For this purpose, the biosensor may comprise an insertable portion. Herein, the term "insertable portion" may generally refer to a part or component of an element configured to be insertable into an arbitrary body tissue. Preferably, the biosensor may fully or partially comprise a biocompatible surface, i.e., a surface which may have as little detrimental effects on the user, the patient, or the body tissue as possible, at least during typical durations of use. For this purpose, the insertable portion of the biosensor may have a biocompatible surface. In accordance with this disclosure, the biosensor, specifically the insertable portion thereof, is fully or partially covered with at least one biocompatible membrane, such as at least one polymer membrane or gel membrane which, on one hand, may be permeable for the body fluid or at least for the analyte as comprised therein and which, on the other hand, retains sensor substances, such as one or more test chemicals within the sensor, thus preventing a migration thereof into the body tissue. Other parts or components of the biosensor may remain outside of the body tissue.

As generally used, the terms "patient" and "user" may refer to a human being or an animal, independent from whether the human being or animal, respectively, may be in a healthy condition or may suffer from one or more diseases. As an example, the patient or the user may be a human being or an animal suffering from diabetes. However, additionally or alternatively, this disclosure may be applicable to other types of users, patients or diseases.

As further used herein, the term "body fluid" may, generally, refer to a fluid, in particular a liquid, which may typically be present in a body or a body tissue of the user or the patient and/or which may be produced by the body of the user or the patient. Preferably, the body fluid may be selected from the group consisting of blood and interstitial fluid. However, additionally or alternatively, one or more other types of body fluids may be used, such as saliva, tear fluid, urine or other body fluids. During the detection of the at least one analyte, the body fluid may be present within the body or body tissue. Thus, the biosensor may, specifically, be configured for detecting the at least one analyte within the body tissue.

As further used herein, the term "analyte" may refer to an arbitrary element, component, or compound being present in the body fluid, wherein the presence and/or the concentration of the analyte may be of interest to the user, the patient, or to a medical staff, such as to a medical doctor. Particularly, the analyte may be or may comprise at least one arbitrary chemical substance or chemical compound which may participate in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may, in particular, be an analyte-specific detection. Without restricting further possible applications, this disclsoure is described in the following with particular reference to a monitoring of glucose in an interstitial fluid. As generally used, at least one property of the analyte may be characterized by a "value" related to this property, such as a concentration, of the analyte. However, other kinds of properties may also be feasible, such as interfering substances or "interferents," i.e., additional redox active substances comprised by the body fluid which may be oxidized in a similar manner and may, thus, generate further electrons which may be detectable as an additional current.

As further used herein, the term "measuring" refers to a process of generating at least one signal, in particular at least one measurement signal, which characterizes an outcome of at least one measurement. Specifically, the at least one signal may be or may comprise at least one electronic signal, such as at least one voltage signal and/or at least one current signal, in particular a raw current signal. The at least one signal may be or may comprise at least one analogue signal and/or may be or may comprise at least one digital signal. Especially in electrical systems, it may be required to apply a prespecified signal to a specific device in order to be able to record the desired measurement signal. By way of example, measuring a raw current, in particular according to method step b), may require the application of a voltage signal to the device, or vice-versa.

In addition, the term "measuring" as used herein, further, refers to generating an additional value related to the measurement signal, wherein the respective measurement signal may be influenced by a variable being capable of influencing the measurement signal. As used herein, the sensitivity S of the biosensor may, thus, be measured by measuring the raw current I of the biosensor, whereby a concentration c of an analyte, such as of glucose, may be taken into account. In an ideal representation, the sensitivity S of the biosensor may, generally, defined by Equation (1):

$$S=(I-I_0)/c, \quad (1)$$

wherein the term $I_0$ refers to a possible zero current, which may originate from interferents. In practice, Equation (1) may hold true for a concentration below an empirical value of 100 mg/dl to 150 mg/dl glucose, wherein the sensitivity S of the biosensor may exhibit a more complex curvature for concentrations above this empirical value. In practice, the raw current I may be measured and the sensitivity may, subsequently, be corrected in case of a sensitivity drift. Alternatively, the value of the raw current I may be corrected in this case.

Further according to this disclosure, an in-vivo current response which is indicative of the in-vivo admittance Y(t) of the biosensor is measured according to method step c). As generally used, the term "in-vivo" refers to an actual state of the biosensor during its application to the patient or user which may, especially, be in contrast to a state of the biosensor as manufactured or as initially provided to the patient or user. In particular, the in-vivo current response I(t) may be determined by applying a time-varying voltage U(t) to the biosensor. As generally known, the admittance Y(t) of the biosensor may be defined by Equation (2):

$$Y(t)=I(t)/U(t)=Y'(t)+iY''(t), \quad (2)$$

wherein the terms Y'(t) and Y''(t) refer to time-varying real and imaginary parts of the complex admittance Y(t), respectively. As an alternative or in addition, a reciprocal value of the admittance, which is, in general, denoted as "impedance" of the biosensor, may be measured. For further details with regard to preferred procedures for actually measuring the in-vivo current response indicative of the in-vivo admittance Y(t) of the biosensor reference may be made to the description below.

As further used herein, the term "determining" relates to a process of generating at least one representative result, such as a plurality of representative results, by using at least one signal, in particular at least one measurement signal, which characterizes an outcome of the measurement. As used herein, a sensitivity-to-admittance relation may, thus, be determined by providing at least one selected relation between the sensitivity S and the admittance Y(t) of the biosensor, wherein at least one measured value for the sensitivity S of the biosensor and at least one measured value for the admittance Y(t) of the biosensor may be used for this purpose. As generally used, the selected "relation" between two values, such as the sensitivity S and the admittance Y(t), may be provided by applying an operation, such as a mathematical operation, between at least one first value, such as related to the sensitivity S, and at least one second value, such as related to the admittance Y(t). By way of example, the mathematical operation may be selected from at least one of a ratio, a weighted ratio, or a functional ratio, wherein the weighted ratio refers to a ratio in which each term is subject to a prior weighing, and wherein the functional ratio refers to a ratio in which each term, prior to forming the ratio, is subjected to a function, such as a polynomic function, an exponential function or a logarithmic function. However, other kinds of operations and functions may also be feasible. In a preferred embodiment, the sensitivity-to-admittance relation may be a sensitivity-to-admittance ratio S(t)/Y(t) which may, preferably, be determined by forming a ratio of the sensitivity S with regard to the admittance Y(t), wherein at least one measured value for the sensitivity S of the biosensor and at least one measured value for the admittance Y(t) of the biosensor may be used. However, other kinds of relations may also be feasible for this purpose.

As further used herein, the term "monitoring" refers to a process of continuously recording data and deriving desired information therefrom without user interaction. For this purpose, a plurality of measurement signals are generated and evaluated, wherefrom the desired information is determined. Herein, the plurality of measurement signals may be recorded within fixed or variable time intervals or, alternatively or in addition, at an occurrence of at least one prespecified event. In particular, the biosensor according to this disclosure may, especially, be adapted for the continuous monitoring of one or more analytes, in particular of glucose, such as for managing, monitoring, and controlling a diabetes state.

The biosensor according to this disclosure is an electrochemical or an amperometric sensor. As used herein, the terms "electrochemical sensor" or "amperometric sensor" both refer to a sensor being adapted for performing at least one electrochemical measurement, in particular a plurality or series of electrochemical measurements, in order to detect the at least one substance as comprised within the body fluid by using an amperometric method. Especially, the terms "electrochemical measurement" or "electrochemical measurement" refers to a detection of an electrochemically detectable property of the substance, such as an electrochemical detection reaction, by employing amperometric methods. Thus, for example, the electrochemical detection reaction may be detected by applying and comparing one or more electrode potentials. Specifically, the electrochemical sensor may be adapted to generate at least one electrical sensor signal which may directly or indirectly indicate a presence and/or an extent of the electrochemical detection reaction, such as at least one current signal and/or at least one voltage signal. The measurement may be a qualitative and/or a quantitative measurement. Still, other embodiments are feasible.

For this purpose, the electrochemical sensor as used herein is arranged in a fashion of an electrochemical cell and, thus, employs at least one pair of electrodes. As generally used, the term "electrode" refers to an entity of the test element which is adapted to contact the body fluid, either directly or via at least one semipermeable membrane or layer. With regard to this disclosure, at least one of the electrodes is covered by a membrane, wherein this electrode may be embodied in a fashion that an electrochemical reaction may occur at at least one surface of this electrode. In particular, this electrode may be embodied in a manner that oxidative processes and/or reductive processes may take place at selected surfaces of the electrode. In a particularly preferred embodiment as used herein, the biosensor has a working electrode, a reference electrode, and a counter electrode, wherein both the working electrode and the reference electrode may be covered by a membrane, wherein—in contrast to the reference electrode—the working electrode further includes an enzyme, wherein the working electrode may comprise the enzyme or may be covered by an enzyme layer. The counter electrode may, additionally, be covered by a membrane or not. However, other embodiments having a different number of electrodes or a different number of electrodes covered by a membrane may also be feasible.

More particular, the electrochemical sensor may be a multiple field sensor, wherein the working electrode may cover more than one field, such as 4, 8, 12, or 16 fields on a substrate, such as a polyimide substrate, while the counter electrode may be placed on a back side of the substrate. Preferably, the working electrode may comprise a composition of carbon paste, $MnO_2$ particles as catalyst and/or mediator, and glucose oxidase (GOD) and/or glucose dehydrogenase (GDH) applied to an electrically conducting layer, such as a gold and/or a copper layer, deposited on the substrate, while the counter electrode may, preferentially, be or comprise a gold electrode and the reference electrode an Ag/AgCl electrode. Further, the membrane which covers the working electrode may comprise two individual partial membranes which may be stacked on top of each other. Herein, a first partial membrane which may be located adjacently to the working electrode may constitute a diffusion barrier which, in particular, may be a hydrophilic layer, such as hydrophilic polyurethane having both hydrophilic and hydrophobic side chains. In contrast hereto, a second partial membrane which may be placed on top of the first partial membrane and may, thus, adjoin the volume adapted for receiving the body fluid may be a biocompatible layer which, preferably, may comprise a biogel, such as a polyacrylate block copolymer having a hydrophobic backbone and hydrophilic side chains. In particular, both partial membranes may be applied by using a dip coating process.

Further, the working electrode, the reference electrode, and the counter electrode may, preferably, be connected via a potentiostat, wherein an electrical potential difference may be applied via the potentiostat between the working electrode and the reference electrode. Thus, the detailed course of a redox reaction may be detected here by comparing one or more electrode potentials, in particular an electrical potential difference between the working electrode and the reference electrode. As used herein, the term "potentiostat" refers to an electronic device which is adapted for adjusting and/or measuring the electrical potential difference between two of the electrode in the electrochemical cell, in particular, between the working electrode and the reference electrode. For this purpose, the potentiostat may be implemented in order to be capable of injecting a current into the electrochemical cell through the counter electrode, which is, for this reason, also denoted as an auxiliary electrode. This setup of the potentiostat may allow both adjusting the electrical potential difference between the working electrode and the reference electrode within the electrochemical cell and, alternatively or in addition, measuring the raw current I, preferably between the working electrode and the counter electrode. Additionally, the potentiostat may equally be employed for measuring a raw current I, whereby no potential drop may occur due to an active current regulation of the potentiostat. As a result, the potentiostat may apply a voltage, such as a direct or an alternating voltage, preferably a direct voltage, between the working electrode and the reference electrode and, preferably simultaneously, measure, preferably, the direct or, alternatively, the alternating raw current I generated thereby between the working electrode and the counter electrode. As a result, the biosensor may be capable of measuring the raw current I between the working electrode and the reference electrode. Further, the sensitivity S may be obtained from a temporal course of the raw current I with respect to the concentration c of the analyte. As described below in more detail, a further circuit may, preferably, be used for determining the in-vivo current response which is indicative of the in-vivo admittance $Y(t)$ of the electrochemical cell, whereby, in addition, the complex admittance $Y(t)$ of the electro-chemical cell or a value related hereto may be measured.

The working electrode may further include an enzyme or, alternatively, may be covered by an enzyme layer, wherein the enzyme or the enzyme layer may be or comprise a test chemistry, while the reference electrode and the counter electrode may, preferably, be maintained free from the test chemistry. Generally, the term "test chemistry" refers to an arbitrary material or a composition of materials being adapted to change at least one detectable property in the presence of the at least one analyte, wherein the detectable property is selected here from the above-mentioned electrochemically detectable property. Specifically, the at least one test chemistry may be a highly selective test chemistry, which only changes the property if the analyte is present in the sample of the body fluid applied to the test element, whereas no change occurs if the analyte may not be present. More preferably, the degree or change of the at least one property may be dependent on the concentration of the analyte in the body fluid, in order to allow for a quantitative detection of the analyte. As used herein, the test chemistry may comprise one or more enzymes, such as glucose oxidase (GOD) and/or glucose dehydrogenase (GDH), preferably an enzyme which, by itself and/or in combination with other components of the detector substance, is adapted to perform an oxidative process or a reductive process with the at least one analyte to be detected. Additionally or alternatively, the test chemistry may comprise one or more auxiliary components, such as one or more co-enzymes and/or may comprise one or more catalysts and/or redox mediators. Additionally, the test chemistry may comprise one or more dyes, which, preferably in interaction with the one or more enzymes, may change their color in the presence of the at least one analyte to be detected.

In a particularly preferred embodiment of this disclosure, the biosensor may be a diffusion-controlled biosensor, in particular a diffusion-controlled amperometric biosensor. As generally used, the term "diffusion" refers to a net movement of a substance, such as molecules or particles, in a fluid down a concentration gradient from a region comprising a high concentration of the substance to a region of low concentration of the substance. Not wishing to be bound by theory, in the biosensor the diffusion of the analyte, such as glucose, from the body fluid to a surface of the working electrode may be considered as a rate limiting step in a typical concentration range. Herein, the biosensor may be denominated as "diffusion-controlled" in a regime in which a ratio of a diffusion rate to a reaction rate of the analyte may be adjusted in a manner that a reaction of the analyte arriving at the surface of the working electrode with the enzyme and further steps following the reaction, such as an electron transfer, may occur so rapidly that the concentration of the analyte at the surface of the working electrode may vanish. This regime can, in particular, be achieved by a combination of the enzyme being present at the surface of the working electrode in excess and of membrane transport properties, in particular a thickness and a permeability of the membrane. As a result, a well-adjusted diffusion-controlled biosensor may, thus, exhibit a high linearity of the sensitivity with respect to the analyte concentration c according to Equation (1) while a drift of the sensitivity S, which may, in particular, occur due to a drop or loss of enzyme activity as a result of measuring time or storage time, can be avoided. Consequently, the sensitivity S of the biosensor may, therefore, depend on the membrane transport properties, in particular on the thickness and the permeability of the membrane. In other words, changes of the membrane properties may be considered as responsible for changes of the sensitivity S.

On the other hand, it may be feasible to investigate the membrane properties by employing a dielectric characterization of the biosensor. In particular, static experiments have shown a good correlation between the sensitivity S and an electrical resistance or conductance of the membrane. As generally used, the electrical conductance of the membrane relates to a reciprocal of the electrical resistance $R_M$ of the membrane in case of a DC circuit. Herein, a good correlation between ion diffusion and glucose diffusion could be demonstrated in all swelling states of the membrane as long as the enzyme was present in excess, the ion concentration remained constant, and the temperature stayed constant.

Not wishing to be bound by theory, a functional testing of the biosensor may, thus, provide a tendency for the sensitivity S, wherein the permeability $P_{ana}$ of the membrane concerning the analyte, a thickness d of the membrane, and a geometric area A of the electrode can be taken into account according to the Equation (3):

$$S = (I - I_0)/c \sim P_{ana}/d \cdot A \qquad (3)$$

the $\sim$ sign denoting a proportionality between the sensitivity S, on one hand, and the ratio of the permeability $P_{ana}$ of the membrane concerning the analyte with respect to the product of the thickness d of the membrane and the surface area A of the electrode, on the other hand.

Further, a capacitance of a double layer may be formed at a surface of the working electrode which may be maintained at frequencies of 0.01 Hz and to 1 MHz, preferably of 0.1 Hz to 100 kHz, more preferred of 1 Hz to 10 kHz, in particular of 10 Hz to 1 kHz. As a result, a measurement of the admittance Y(t) may not be determined by Faraday currents, including but not limited to the zero currents, but may, predominantly, refer to a conductivity of ions, such as Na$^+$ or Cl$^-$, in the membrane. Thus, the dielectric characterization of the biosensor may provide a following tendency for the admittance Y(t), wherein the permeability $P_{ion}$ of the membrane with respect to the ions, the thickness d of the membrane, and an actual surface area A of the electrode can be taken into account according to Equation (4):

$$Y(t) \sim P_{ion}/d \cdot A \qquad (4)$$

Consequently, the sensitivity-to-admittance relation S(t)/Y(t) can be estimated to depend only on a ratio of the respective membrane permeabilities $P_{ana}$, $P_{ion}$ which are, respectively, related to the analyte and the ions in accordance with Equation (5):

$$S(t)/Y(t) \sim P_{ana}/P_{ion} \qquad (5)$$

As a result, the sensitivity-to-admittance relation S(t)/Y(t) can be employed in order to provide information about a current state of the intrinsic membrane transport properties while geometric properties related to the membrane, in particular the thickness d of the membrane and the surface area A of the working electrode, can be disregarded. Thus, by determining the sensitivity-to-admittance relation S(t)/Y(t), a change of permeability and thickness of the membrane, such as by a swelling of the membrane during an operation of the biosensor may, advantageously, be negligible. In other words, the sensitivity-to-admittance relation S(t)/Y(t) may be assumed to stay constant during the operation of the biosensor as long as the biosensor can be considered as a diffusion-controlled biosensor. As mentioned above, the term "diffusion-controlled" refers to a biosensor in which the reaction rate of the analyte may be considerably higher compared to the diffusion rate of the analyte. As a result, no in-vivo drift may occur in the biosensor, wherein the term "in-vivo drift" relates to a change of the sensitivity of the biosensor due to a change of in-vivo properties of the biosensor, such as of the membrane properties, in particular of the intrinsic membrane properties, during the in-vivo operation of the biosensor.

According to step c), the raw current I and the in-vivo current response being indicative of the in-vivo admittance of the biosensor is measured at two different operating points, i.e., at a first operating point and at a second operating point. As used herein, the term "operating point" refers to a particular state of the biosensor which may be achieved by applying a definite state of the electronics unit to the biosensor. In accordance with this disclosure, the first operating point is selected for providing a first characteristic value which is related to the electrical resistance of the membrane while the second operating point is selected for providing a second characteristic value which is related to the electrical capacitance of the working electrode. As further used herein, the term "characteristic value" refers to a numerical value which is related to the operating point and which provides representative information of the state of the biosensor at the corresponding operating point.

As described below in more detail, the first characteristic value may, preferably, comprise a value which may be related to, especially being proportional to, the electrical resistance of the membrane, in particular proportional to a geometric area, i.e., a cross section, of the working electrode carrying the membrane, to the thickness of the membrane, and to the permeability of the membrane with respect to at least one kind of ions. With respect to the thickness and/or the permeability of the membrane, reference may be made to the description elsewhere in this document. Similarly, the second characteristic value may comprise a value that may be related to, especially being proportional to, a reciprocal of the electrical capacitance of the working electrode, in particular being proportional to an actual surface area of the working electrode carrying the membrane and to the amount of catalyst and/or mediator available in the membrane. With respect to the catalyst and/or the mediator, reference may be made to the description elsewhere in this document. However, other kinds of characteristic values may also be feasible.

As generally used, the term "geometric area of an electrode" refers to a measured size of the electrode which depends on the physical dimensions of the body as used for the electrode and is, thus, expected not to alter during the operation of the biosensor. In contrast hereto, the term "actual surface area of an electrode" refers to a partition of the surface of the electrode which actually carries the membrane. As a result, the actual surface area of the electrode may be identical with the geometric area of the electrode as long as the geometric area of the electrode is completely covered by the membrane. However, the actual surface area of the electrode may be subject to alterations during the operation of the biosensor, in particular, in an event in which the electrode chemistry may at least partially be detached from the electrode pad, which can be considered as active electrode surface after detachment of the electrode chemistry. In this event, a ratio of the surface of the electrode vs. the diffusion area as determined by the electrode pad may remain whereas an influence of roughness and pseudo capacity of the electrode paste can be disregarded. Thus, this procedure allows taking into account the different kinds of areas being present in the biosensor in determining the corresponding in-vivo properties of the biosensor. In particular, this procedure, advantageously, allows using a value which does not depend on an actual area of the electrode for interpreting the swelling of the membrane during the operation of the biosensor.

According to method step a), the reference sensitivity-to-admittance relation of the biosensor may, in general, be provided for further reference. For this purpose, the reference sensitivity-to-admittance relation may, preferably, be determined at least once by applying a calibration procedure for which, preferably, a known biosensor, such as a common test strip, may be employed for a spot measurement. Preferably, the calibration procedure may be performed as a reduced "multiple calibration," in particular in form of a regular calibration of the biosensor or a calibration upon an event, such as a request of a patient actually wearing the biosensor or following a prespecified incident. More preferred, the calibration procedure may be performed as an "initial calibration" by calibrating the biosensor during an initial phase, preferably a single time, with the particular patient who is actually wearing the biosensor before the initial in-vivo operation of the biosensor at the patient. However, mostly preferred, the calibration procedure may be performed as a "factory calibration" which comprises calibrating the biosensor in a manufacturing facility, in particular by using an in-vitro operation of the biosensor, which is independent from the patient who is going to wear the particular biosensor, thus, advantageously avoiding an invasive spot measurement on any patient. However, other possibilities are conceivable. Independently from the chosen calibration procedure, the reference sensitivity-to-admittance relation, thus, allows determining the actual intrinsic membrane properties in comparison to the intrinsic membrane properties as investigated under prespecified conditions, wherein, if applicable, the most recently determined sensitivity-to-admittance relation may, preferably, be used for the purposes of step d).

In accordance with this disclosure, the in-vivo properties of the biosensor are, thus, being detected. As used herein, the term "in-vivo properties" refers to actual physical and chemical properties of a particular biosensor which represent the actual state of the particular biosensor during an in-vivo determining of the analyte value in the sample of the body fluid and which may be capable of influencing the analyte value as determined by the particular biosensor in the particular state. As indicated above, the physical and chemical properties of the particular biosensor may include but be not limited to the properties, in particular the intrinsic properties, of the membrane which covers the working electrode. Further kinds of properties which may be capable of influencing the analyte value are described below in more detail.

According to step d), the analyte value in the sample of the body fluid is, thus, determined, on one hand, by using the raw current and by compensating an in-vivo drift in the sensitivity of the biosensor as described below and, on the other hand, by taking into account at least the first characteristic value but, preferably, also the second characteristic value. In particular, the first characteristic value and, preferably, also the second characteristic value are taken into account for this purpose in a first respect according to step d) while, in a second respect according to step e), a failsafe operation of the biosensor is, further, taken into account, wherein the failsafe operation is based, as described below in more detail, on at least one of the first characteristic value and the second characteristic value. More particular, whereas the first characteristic value which is related to the reciprocal of the electrical resistance of the membrane is used according to this disclosure in any event, the second characteristic value which is related to the electrical capacitance of the working electrode, may, due to its independence of the different kinds of areas being present in the biosensor as described above, especially, be useful in improving a correlation between the raw current and the analyte value.

According to this disclosure, the in-vivo sensitivity drift in the biosensor may be compensated by correcting an actually determined value for the sensitivity by using the first characteristic value and, preferably, also the second characteristic value of the in-vivo admittance, whereby the value of the sensitivity-to-admittance relation as provided during step a) is taken into account. According to Equation (1), the raw current I may vary depending on the sensitivity S of the biosensor, wherein the sensitivity S of the biosensor, which appears to be temperature and time dependent, may decay over shelf life, such as due to a membrane reorganization depending on the storage conditions, but may increase during in-vivo operation of the biosensor, such as due to swelling of the membrane. In this manner, the in-vivo sensitivity drift in the biosensor may, in particular, relate to an alteration of intrinsic membrane properties of the membrane which covers the working electrode of the biosensor over time or in consequence of an unexpected event, and thus may influence the determination of the analyte value from the raw current I.

As further used herein, the term "compensating" relates to a process of modifying a measured value which is capable of being influenced by a side effect, for which purpose an additional consideration is applied by which the side effect may be diminished or, particularly preferred, completely extinguished, wherein the additional consideration may, in particular, be based on additional measurement results on the same biosensor. As used herein, an in-vivo sensitivity drift in the biosensor is capable of influencing the raw current I and is, thus, in accordance with method step d), being compensated by taking into account a first characteristic value and, preferably, of a second characteristic value as defined above. For the purpose of determining both the first characteristic value and the second characteristic value, the in-vivo current response indicative of the in-vivo admittance of the biosensor is measured at two different operating points as described elsewhere in this document. In a preferred embodiment, the in-vivo sensitivity drift in the biosensor may, thus, be compensated by correcting the measured value for the raw current by determining an actual value of the sensitivity by using the first characteristic value and, preferably, the second characteristic value, whereby the value of the sensitivity-to-admittance relation as provided during step a) is taken into account. However, other manners of deriving the compensation may also be applicable.

However, in contrast to the state of the art where only a temporal drift of the sensitivity S(t) may be measured and the biosensor may be calibrated after a predefined time interval may have passed and/or when the temporal drift of the sensitivity S(t) may have exceed a given threshold, this disclosure allows, concurrently, taking into account a temporal variation of the admittance Y(t) with respect to the temporal drift of the sensitivity S(t). As particularly described by Equation (5), the in-vivo sensitivity-to-admittance ratio S(t)/Y(t) may be insensitive to a number of variations in the biosensor during the in-vivo operation and may, thus, be unaltered despite a concurrent alteration of the sensitivity S(t) alone. However, as particularly expressed by the actual operating mechanism of the biosensor behind Equation (5), recalibrating the biosensor after a predefined time interval and/or the temporal drift of the sensitivity S(t) exceeding a given threshold may, thus, no longer be required. As a result, the present method may, compared to the state of the art, allow reducing a number of calibrations and, moreover, to be capable of relying on an initial calibration or, more preferred, on a factory calibration of the biosensor. Based on these considerations, the present method may, in addition, also be applied for monitoring a failsafe operation of the biosensor, which is described below in more detail.

In a particularly preferred embodiment of this disclosure, measuring the in-vivo current response indicative of the in-vivo admittance Y(t) of the biosensor may be implemented by an application of a non-faradaic method, in particular, by applying at least one potential step to the electrical potential difference at the biosensor, especially between the working electrode and the reference electrode. For this purpose, the potentiostat may preferably be used. As used herein, the term "potential step" may refer to an impingement of the working electrode comprising the membrane by an additional electrical potential which may be provided in form of an electrical pulse. Herein, the additional electrical potential may, preferably, be provided by an electrical pulse over a time interval of 10 µs, more preferred of 50 µs, to 1000 µs, more preferred of 250 µs, especially of approximately 100 µs, after the application of the potential step.

Thereby, a height of the potential step may be selected in order to define one of a maximum voltage $U_{max}$ or a maximum current $I_{max}$, which may be applied to the membrane of the biosensor. By way of example, the potential step may comprise an application of an enhanced or diminished electrical potential $E_2$ over a time interval $\Delta t$ with respect to the electrical potential $E_1$ prevailing at the membrane, thus proving an electrical potential difference $\Delta E$ to the membrane over the time interval $\Delta t$. In this regard, it may be emphasized that the sign of the potential step may be selected as being positive or negative. Herein, the electrical potential difference $\Delta E$ may, preferably, provide an additional voltage of 10 mV to 500 mV, more preferred of 50 mV to 100 mV to the prevailing electrical potential $E_1$.

However, other kind of measures which may be capable of providing a time-varying electrical potential to the biosensor may also be feasible. As used herein, these kinds of measures may also be comprised by the term "potential step." In particular, a time-varying waveform, be it a sine or a cosine wave or a linear or a non-linear combination of sine and/or cosine waves, at least one linear or non-linear sweep, at least one cyclically varying signal, such as provided by voltammetry, may also be applicable, as long as it may allow determining the in-vivo current response indicative of the in-vivo admittance Y(t) of the biosensor. As a further alternative, the in-vivo current response of the biosensor may be determined by application of an alternating current signal.

Taking further into consideration a capacitance C of the working electrode, the current I(t) response after application of the potential step may follow an exponential decay of $$I(t) = \frac{E_2 - E_1}{R_M} e^{-\frac{t}{R_M \cdot C}} + \frac{E_2}{R_D} \quad (6)$$

or $$I(t) = I_{max} \cdot e^{-\frac{t}{\tau}} + I_0 \quad (7)$$

wherein $I_{max}$ denotes a maximum current, $I_0$ the zero current, $R_M$ an electrical resistance of the membrane, $R_D$ an electron transfer resistance and the term $$\tau = R_M \cdot C \quad (8)$$

a time constant $\tau$ which may be assigned to the decay of the current due to the potential step, thus being indicative of the in-vivo admittance Y(t) of the biosensor.

As a further result, the following relationships emerge:

$$R_M = \Delta E / I_{max}, \quad (9)$$

$$C = \tau/R_M, \quad (10)$$

and $$C = Q/\Delta E, \quad (11)$$

wherein the term $$Q = \int I(t)dt \quad (12)$$

denotes the additional charge provided to the electrode surface via the potential step.

In accordance with this disclosure, these kinds of measurement may be performed at using two different operating points which may, preferably, be selected by observing the in-vivo current response at two different time constants. According to Equation (8), the time constant τ is determined by the electrical capacitance C of the working electrode and the electrical resistance $R_M$ of the membrane by $$\tau = R_M \cdot C \quad (8)$$

In a particularly preferred embodiment, the first operating point may, thus, be selected below τ while the second operating point may be selected above τ, preferably above 2τ, 3τ, 4, or 5τ. As a result, the first operating point reflects the first characteristic value which is related to the electrical resistance of the membrane, thus, providing information about the geometric area of the working electrode carrying the membrane, the thickness of the membrane, and the permeability of the membrane with respect to at least one kind of ions while the second operating point reflects the second characteristic value which is related to the electrical capacitance of the working electrode, thus, providing information about the actual surface area of the working electrode carrying the membrane and the amount of catalyst and/or mediator available in the membrane. Accordingly, the second operating point may be selected in dependence of the architecture of the biosensor, preferably, depending on a membrane thickness and/or a mediator load. In addition, further considerations may be conceivable. Consequently, this kind of measurement may be adapted to integrally taking into account all different thicknesses of the membrane which might occur during swelling and de-swelling of the membrane.

In relationship to determining the analyte value in the sample of the body fluid, the present method is, concurrently, used for monitoring the failsafe operation of the biosensor. As generally used, the term "failsafe operation" refers to a mode of operation of the biosensor which comprises a detection of malfunction in the biosensor which may be capable of influencing the analyte value, wherein the malfunction may be caused by a structural modification of the biosensor during its operation over a period of time and/or by loss of substances as required for the operation of the biosensor, such as catalyst, mediator and/or enzyme activity. Preferably, the failsafe operation comprises a mode of operation of the biosensor selected from at least one of an indication of no valid value, a recommendation for recalibration, and a request for shut-off of the biosensor. For this purpose, the sensitivity S, the electrical capacitance C of the working electrode, and the electrical resistance $R_M$ of the membrane may be determined, wherein the electrical capacitance C of the working electrode and the electrical resistance $R_M$ of the membrane, according to Equation (8), are related to each other by time constant τ. In particular, a structural modification of the biosensor may, thus, be determined by combining alterations of at least two of the sensitivity S, the electrical capacitance C of the working electrode, and the electrical resistance $R_M$ of the membrane.

Exemplary embodiments which are particularly suited for monitoring the failsafe operation of the biosensor are presented below.

In a particularly preferred embodiment, both the analyte value in the sample of the body fluid and the information regarding the failsafe operation of the biosensor may be presented to the patient or user in a predefined format. Herein, the analyte value may be displayed in explicit form, preferably in mg/dl and/or as a curve illustrating a temporal variation of the analyte value. Instead of indicating or displaying a definite result acquired with regard to the failsafe operation of the biosensor, a sensitivity drift compensation may be performed without explicitly informing the patient or the user while a flag related to a proposed reaction may be provided. By way of example, in a case in which the biosensor is in a failsafe operational mode, a flag indicating "valid value" can be displayed whereas, in a case in which the biosensor is outside a failsafe operational mode, a flag selected from one of "no valid value," "recalibration required," or "shut-off" may be displayed instead. However, further ways of illustrating the obtained results may also be feasible.

As further mentioned above, the biosensor as used herein may be a fully implantable biosensor or, alternatively, a partially implantable biosensor. In particular, the biosensor may be adapted for a continuous monitoring of the analyte in the body fluid, preferably for a continuous measurement of the analyte in a subcutaneous tissue, in particular in an interstitial fluid, such as blood. However, other kinds of biosensors as well as of applications of the biosensor may also be feasible. As further mentioned above, the analyte may, preferably, comprise glucose, wherein the enzyme may be glucose oxidase (GOD). Alternatively, other kinds of enzymes, such as glucose dehydrogenase (GDH), may also be employed.

In a further aspect of this disclosure, an electronics unit for detecting the in-vivo properties of the biosensor by for performing the method as described above is disclosed. For this purpose, the electronics unit is, in interoperation with the biosensor, adapted for electrochemically determining at least one value of an analyte in a sample of a body fluid, wherein the electronics unit is further adapted for measuring the raw current and the current response being indicative of the admittance of the biosensor.

As used herein, the term "electronics unit" may refer to an arbitrary device, preferably to an electronic device, which may be handled independently from the biosensor. The electronics unit may, especially, be adapted to interact with the biosensor in order to apply a voltage to at least one of the electrodes and to, concurrently or subsequently, detect the least one signal produced by one of the electrodes of the biosensor. For this purpose, the electronics unit may be configured to apply the at least one electric pulse and/or to perform the at least one impedance measurement as described above and/or below. For this purpose, the electronics unit may, particularly, be adapted for applying an electrical potential between the at least one working electrode and the at least one reference electrode of the biosensor and for measuring the raw current generated thereby, preferably, between the working electrode and the at least one counter electrode of the biosensor.

The electronics unit may, further, be configured to perform the at least one amperometric measurement by using the electrodes of the biosensor, in particular, to detect at least one direct current signal and at least one current response, preferably, concurrently or subsequently. For this purpose, the electronics unit may, especially, be configured to be capable of applying both a prevailing electrical potential and a potential step to the electrodes of the biosensor and to detect a response as described elsewhere herein. In particular, the electronics unit may, thus, comprise a direct current measuring unit and comprises a potential step response measuring unit, wherein the direct current measuring unit may be configured for measuring the raw current while the potential step response measuring unit is configured for measuring the in-vivo current response indicative of the in-vivo admittance of the biosensor. For this purpose, the potential step response measuring unit comprises at least a charge counter and a peak detector. However, other embodiments may also be feasible.

The electronics unit may, further, be adapted to derive at least one item of information regarding an analyte value related to the analyte in the sample of the body fluid from this detection. For this purpose, the electronics unit may comprise at least one electronic evaluation device interacting with the electrodes, in particular, in order to derive the at least one analyte value from the at least one signal. Thus, the electronics unit may comprise at least one evaluation device comprising at least one data processing device, such as one or more of a microcontroller, an application-specific integrated circuit (ASIC), a Field-Programmable Gate Array (FPGA). However, other kinds of devices may also be feasible.

In a further aspect of this disclosure, a system for operating a biosensor for electrochemically detecting at least one analyte value in a sample of a body fluid is disclosed. Accordingly, the system comprises at least one biosensor as described above and/or below which is adapted for electrochemically detecting the at least one analyte value in the sample of a body fluid, wherein the biosensor is operable by performing a method as described above and/or below by using an electronics unit as described above and/or below which is, therefore, adapted for measuring a raw current and determining a sensitivity and an admittance of the biosensor. For this purpose, the electronics unit is configured for compensating the in-vivo sensitivity drift in the biosensor by performing the method as described herein elsewhere.

The method, the electronics unit, and the system according to this disclosure exhibit a number of advantages with respect to the prior art. Compared to the state of the art, the present method may, in particular, allow reducing a number of calibrations and, moreover, to be capable of relying on an initial calibration or, especially preferred, on a factory calibration of the biosensor, such as by determining the sensitivity-to-admittance relation only once by the manufacturer.

Summarizing, the following embodiments are potential embodiments of this disclosure. Other embodiments, however, are feasible.

Embodiment 1: A method for determining at least one analyte value in a sample of a body fluid, wherein a biosensor is, in interoperation with an electronics unit, adapted for electrochemically determining the at least one value of the analyte in the sample of the body fluid, wherein the biosensor comprises at least one working electrode, wherein the working electrode is covered by a membrane and includes an enzyme for providing a reaction with the analyte, wherein the membrane has an electrical resistance and the working electrode has an electrical capacitance, wherein the electronics unit is adapted for measuring a raw current and a current response indicative of an admittance of the biosensor, the method comprising the steps of:

a) providing a sensitivity-to-admittance relation of the biosensor;

b) measuring a raw current in the biosensor;

c) measuring an in-vivo current response indicative of the in-vivo admittance of the biosensor, wherein the in-vivo current response is measured at at least one first operating point and at at least one second operating point, wherein the first operating point is selected for providing a first characteristic value being related to the electrical resistance of the membrane, and wherein the second operating point is selected for providing a second characteristic value being related to the electrical capacitance of the working electrode; and d) determining an analyte value in a sample of a body fluid by using the raw current and compensating an in-vivo sensitivity drift in the biosensor by correcting the measured value for the raw current by determining an actual value of the sensitivity by using the first characteristic value, whereby the sensitivity-to-admittance relation as provided during step a) is taken into account; and e) monitoring a failsafe operation of the biosensor based on the first characteristic value and/or the second characteristic value.

Embodiment 2: A method for detecting in-vivo properties of a biosensor, wherein the biosensor is, in interoperation with an electronics unit, adapted for electrochemically determining at least one value of an analyte in a sample of a body fluid, wherein the biosensor comprises at least one working electrode, wherein the working electrode is covered by a membrane and includes an enzyme for providing a reaction with the analyte, wherein the membrane has an electrical resistance and the working electrode has an electrical capacitance, wherein the electronics unit is adapted for measuring a raw current and a current response indicative of an admittance of the biosensor, the method comprising the steps of:

a) providing a sensitivity-to-admittance relation of the biosensor;

b) measuring a raw current in the biosensor;

c) measuring an in-vivo current response indicative of the in-vivo admittance of the biosensor, wherein the in-vivo current response is measured at at least one first operating point and at at least one second operating point, wherein the first operating point is selected for providing a first characteristic value being related to the electrical resistance of the membrane, and wherein the second operating point is selected for providing a second characteristic value being related to the electrical capacitance of the working electrode; and d) determining an analyte value in a sample of a body fluid by using the raw current and compensating an in-vivo sensitivity drift in the biosensor by considering the first characteristic value and a failsafe operation of the biosensor based on the first characteristic value and/or the second characteristic value.

Embodiment 3: The method according to any one of the two preceding Embodiments, wherein both the first characteristic value and the second characteristic value are considered for determining the analyte value.

Embodiment 4: The method according to any one of the preceding Embodiments, wherein the biosensor at least has at least two electrodes.

Embodiment 5: The method according to the preceding Embodiment, wherein the biosensor at least has a working electrode comprising a membrane, a reference electrode, and a counter electrode, wherein the electrical potential difference is applied between the working electrode and the reference electrode.

Embodiment 6: The method according to the preceding Embodiment, wherein the working electrode, the reference electrode, and the counter electrode are connected via a potentiostat, wherein the electrical potential difference is applied via the potentiostat between the working electrode and the reference electrode.

Embodiment 7: The method according to any one of the preceding Embodiments, wherein the sensitivity of the biosensor is determined from observing a course of the raw current with respect to the analyte value.

Embodiment 8: The method according to any one of the preceding Embodiments, wherein the raw current is measured between the working electrode and the counter electrode.

Embodiment 9: The method according to any one of the preceding Embodiments, wherein the analyte value refers to a concentration of the analyte in the body fluid.

Embodiment 10: The method according to any one of the preceding Embodiments, wherein the sensitivity S of the biosensor is determined by measuring the raw current I of the biosensor, whereby a concentration c of the analyte is taken into account, according to Equation (1)

$$S=(I-I_0)/c, \quad (1)$$

wherein $I_0$ is a possible zero current.

Embodiment 11: The method according to any one of the preceding Embodiments, wherein the first characteristic value comprises a value which is related to, preferably proportional to, the electrical resistance of the membrane.

Embodiment 12: The method according to the preceding Embodiment, wherein the first characteristic value is proportional to a geometric area of the working electrode carrying the membrane, to a thickness of the membrane, and to a permeability of the membrane with respect to at least one kind of ions.

Embodiment 13: The method according to any one of the preceding Embodiments, wherein the second characteristic value comprises a value which is related to, preferably proportional to, the electrical capacitance of the working electrode.

Embodiment 14: The method according to the preceding Embodiment, wherein the second characteristic value is proportional to an actual surface area of the working electrode carrying the membrane and to an amount of catalyst and/or mediator available in the electrode.

Embodiment 15: The method according to any one of the preceding Embodiments, wherein a time constant $\tau$ is determined by the electrical capacitance C of the working electrode and the electrical resistance $R_M$ of the membrane according to Equation (8) by $$\tau = R_M \cdot C \quad (8)$$

wherein the first operating point is selected below $\tau$ and the second operating point is selected above $\tau$.

Embodiment 16: The method according to the preceding Embodiment, wherein the second operating point is selected above one of $2\tau$, $3\tau$, $4\tau$, or $5\tau$.

Embodiment 17: The method according to any one of the preceding Embodiments, wherein the in-vivo current response indicative of the in-vivo admittance of the biosensor is determined by application of at least one time-varying electrical potential between two of the electrodes comprised by the biosensor.

Embodiment 18: The method according to the preceding Embodiment, wherein the in-vivo current response indicative of the in-vivo admittance of the biosensor is determined by application of at least one potential step to the electrical potential difference provided between the two electrodes.

Embodiment 19: The method according to the preceding Embodiment, wherein the at least one potential step comprises applying an additional electrical potential having one of a positive or a negative sign between the two electrodes.

Embodiment 20: The method according to the preceding Embodiment, wherein the additional electrical potential is provided by an electrical pulse over a time interval of 10 µs, preferably of 50 µs, to 1000 µs, preferably of 250 µs, especially of approximately 100 µs, after the application of the potential step.

Embodiment 21: The method according to any one of the two preceding Embodiments, wherein the additional electrical potential is provided by an electrical pulse having an additional voltage of 10 mV to 500 mV, more preferred of 50 mV to 100 mV, in addition to the electrical potential difference.

Embodiment 22: The method according to any one of the preceding Embodiments, wherein the in-vivo current response exhibits a maximum current.

Embodiment 23: The method according to the preceding Embodiment, wherein the maximum current is observed at the first operating point, preferably within a time interval of 10 µs to 100 µs after the application of the potential step.

Embodiment 24: The method according to any one of the two preceding Embodiments, wherein the electrical resistance $R_M$ of the membrane is determined according to Equation (9) by $$R_M = \Delta E / I_{max}, \quad (9)$$

wherein $\Delta E$ is the height of the electrical potential difference applied to the biosensor and $I_{max}$ is the maximum current exhibited by the current response.

Embodiment 25: The method according to any one of the two preceding Embodiments, wherein the electrical capacitance C of the working electrode is determined by observing a temporal course of an accumulated charge Q(t) of the biosensor in consequence of the potential step to the second operating point and by using the height of the electrical potential difference $\Delta E$ applied to the biosensor during the potential step.

Embodiment 26: The method according to any one of the preceding Embodiments, wherein a structural modification of the biosensor is determined by combining alterations of at least two of the sensitivity S, the electrical resistance $R_M$ of the membrane, and the electrical capacitance C of the working electrode.

Embodiment 27: The method according to any one of the preceding Embodiments, wherein the analyte value is displayed in explicit form, preferably in mg/dl and/or as a curve illustrating a temporal variation of the analyte value and wherein, preferably concurrently, in a case in which the biosensor is in a failsafe operational mode, a flag indicating "valid value" is displayed and, in a case in which the biosensor is outside the failsafe operational mode, a flag selected from one of "no valid value," "recalibration required," or "shut-off" is displayed.

Embodiment 28: The method according to any one of the preceding Embodiments, wherein the sensitivity-to-admittance relation is determined by using at least one value for the sensitivity of the biosensor and at least one value for the current response indicative of the admittance of the biosensor are used.

Embodiment 29: The method according to any one of the preceding Embodiments, wherein the failsafe operation comprises a mode of operation of the biosensor selected from at least one of an indication of no valid value, a recommendation for recalibration, and a request for shut-off of the biosensor.

Embodiment 30: The method according to any one of the preceding Embodiments, wherein a calibration of the biosensor is selected from at least one of a multiple calibration, preferably, an initial calibration, and, most preferred, a factory calibration.

Embodiment 31: The method according to any one of the preceding Embodiments, wherein the biosensor is a fully implantable biosensor or a partially implantable biosensor.

Embodiment 32: The method according to the preceding Embodiment, wherein the biosensor is a biosensor for continuously monitoring an analyte.

Embodiment 33: The method according to the preceding Embodiment, wherein the biosensor is a biosensor for a continuous measurement of the analyte in a subcutaneous tissue.

Embodiment 34: The method according to the preceding Embodiment, wherein the biosensor is a biosensor for a continuous measurement of the analyte in a body fluid.

Embodiment 35: The method according to the preceding Embodiment, wherein the biosensor is a biosensor for a continuous measurement of the analyte in an interstitial fluid.

Embodiment 36: The method according to the preceding Embodiment, wherein the biosensor is a biosensor for a continuous measurement of the analyte in blood.

Embodiment 37: The method according to any one of the five preceding Embodiments, wherein the analyte comprises glucose.

Embodiment 38: The method according to the preceding Embodiment, wherein the enzyme is one of glucose oxidase or glucose dehydrogenase.

Embodiment 39: An electronics unit for detecting in-vivo properties of a biosensor by performing a method according to any one of the preceding Embodiments, wherein the electronics unit is, in interoperation with the biosensor, adapted for electrochemically determining at least one value of an analyte in a sample of a body fluid, wherein the biosensor comprises at least one working electrode, wherein the working electrode is covered by a membrane and includes an enzyme for providing a reaction with the analyte, wherein the electronics unit is further adapted for measuring a raw current and a current response indicative of an admittance of the biosensor.

Embodiment 40: The electronics unit according to the preceding Embodiment, comprising a direct current measuring unit and a potential step response measuring unit, wherein the direct current measuring unit is configured for measuring the raw current, and wherein the potential step response measuring unit is configured for measuring the current response indicative of the admittance of the biosensor.

Embodiment 41: The electronics unit according to the preceding Embodiment, wherein the potential step response measuring unit at least comprises a charge counter and a peak detector.

Embodiment 42: The electronics unit according to the preceding Embodiment, wherein the peak detector is configured for measuring a first characteristic value being related to an electrical resistance of the membrane.

Embodiment 43: The electronics unit according to any one of the two preceding Embodiments, wherein the charge counter is configured for measuring a second characteristic value being related to an electrical capacitance of the working electrode.

Embodiment 44: An electronics unit for detecting in-vivo properties of a biosensor by performing a method according to any one of the preceding Embodiments, wherein the electronics unit is, in interoperation with the biosensor, adapted for electrochemically determining at least one value of an analyte in a sample of a body fluid, wherein the biosensor comprises at least one working electrode, wherein the working electrode is covered by a membrane and includes an enzyme for providing a reaction with the analyte, wherein the electronics unit is further adapted for measuring a raw current and a current response indicative of an admittance of the biosensor, wherein the electronics unit comprises a potential step response measuring unit, wherein the potential step response measuring unit is configured for measuring the current response indicative of the admittance of the biosensor, wherein the potential step response measuring unit comprises at least one charge counter and at least one peak detector, wherein the peak detector is configured for measuring a first characteristic value being related to an electrical resistance of the membrane and wherein the charge counter is configured for measuring a second characteristic value being related to an electrical capacitance of the working electrode.

Embodiment 45: The electronics unit according to the preceding Embodiment, wherein the electronics unit comprises a direct current measuring unit, wherein the direct current measuring unit is configured for measuring the raw current.

Embodiment 46: The electronics unit according to any one of the preceding Embodiments referring to the electronics unit, wherein the electronics unit is further adapted for applying an electrical potential between the at least one working electrode and at least one reference electrode of the biosensor and for measuring the raw current generated thereby, preferably between the working electrode and a counter electrode of the biosensor.

Embodiment 47: A system for operating a biosensor for electrochemically detecting at least one analyte value in a sample of a body fluid, the system comprising at least one biosensor for electrochemically detecting at least one analyte value in a sample of a body fluid, wherein the biosensor is operable by performing a method according to any one of the preceding Embodiments referring to a method, and an electronics unit according to any one of the preceding Embodiments referring to an electronics unit.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

Further details of this disclosure may be derived from the following disclosure of preferred embodiments. The features of the embodiments may be realized in an isolated way or in any combination. This disclosure is not restricted to the embodiments. The embodiments are schematically depicted in the figures. Identical reference numbers in the figures refer to identical elements or functionally identical elements or elements corresponding to each other with regard to their functions.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
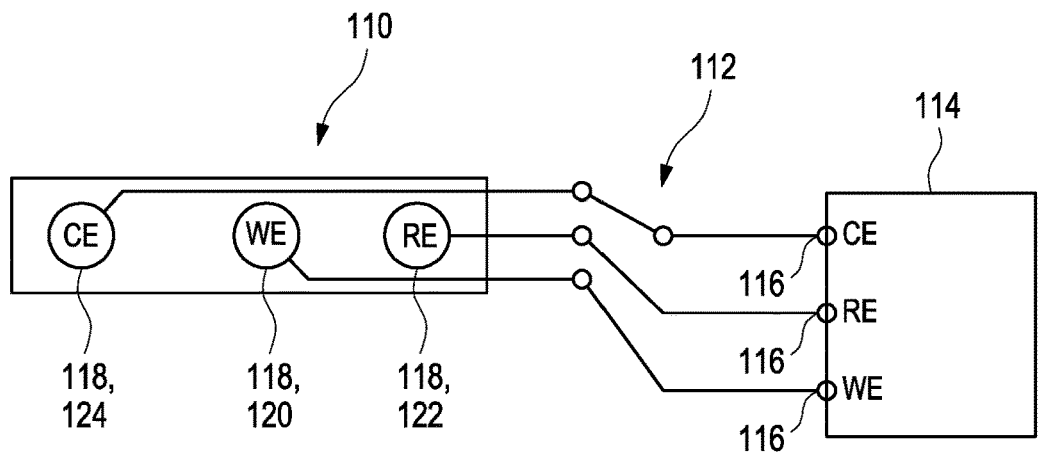
FIG. 1 schematically illustrates an electrical circuit being adapted for determining a sensitivity of a biosensor.

FIG. 1 schematically illustrates a number of aspects related to determining a sensitivity S of a biosensor 110. For a purpose of characterizing the biosensor 110 which constitutes an electrochemical cell as a whole, an electrical circuit 112 as schematically depicted in FIG. 1 may be applicable. Herein, a potentiostat 114 is employed, wherein the potentiostat 114 comprises outputs 116 which are each concurrently connected to one of the electrodes 118 of the biosensor 110, i.e., to a working electrode 120, a reference electrode 122, and a counter electrode 124. The potentiostat 114 may be adapted for adjusting and/or measuring an electrical potential difference between two of the electrodes 118 in the biosensor 110, in particular, between the working electrode 120 and the reference electrode 122. For this purpose, the potentiostat 114 may be implemented in order to be capable of injecting a current into the biosensor 110 through the counter electrode 124. The electrical circuit 112 may, thus, allow both adjusting the electrical potential difference between the working electrode 120 and the reference electrode 122 and, alternatively or in addition, measuring a direct raw current I between the working electrode 120 and the counter electrode 124. As a result, the electrical circuit 112 may be capable of measuring the raw current I between the working electrode 120 and the counter electrode 124.

According to Equation (1), $$S=(I-I_0)/c, \quad (1)$$

wherein the term $I_0$ refers to a possible zero current, the sensitivity S of the biosensor 110 may, further, be obtained from a course of the direct raw current I with respect to a concentration c of an analyte, such as glucose, to be determined by the biosensor 110. Thus, the electrical circuit 112 may be capable of providing an overall response of the biosensor 110 to an analyte profile, such as a glucose profile, as applied to the biosensor 110. However, the DC raw current I cannot differentiate between effects which may arise from different partitions of the biosensor 110 as described below in more detail. In the electrical circuit 112, additional electrochemical techniques for detecting artefacts can only be applied to the working electrode 120 while artefacts related to the reference electrode 122 or the counter electrode 124 may remain undetectable hereby.

Figure 2:
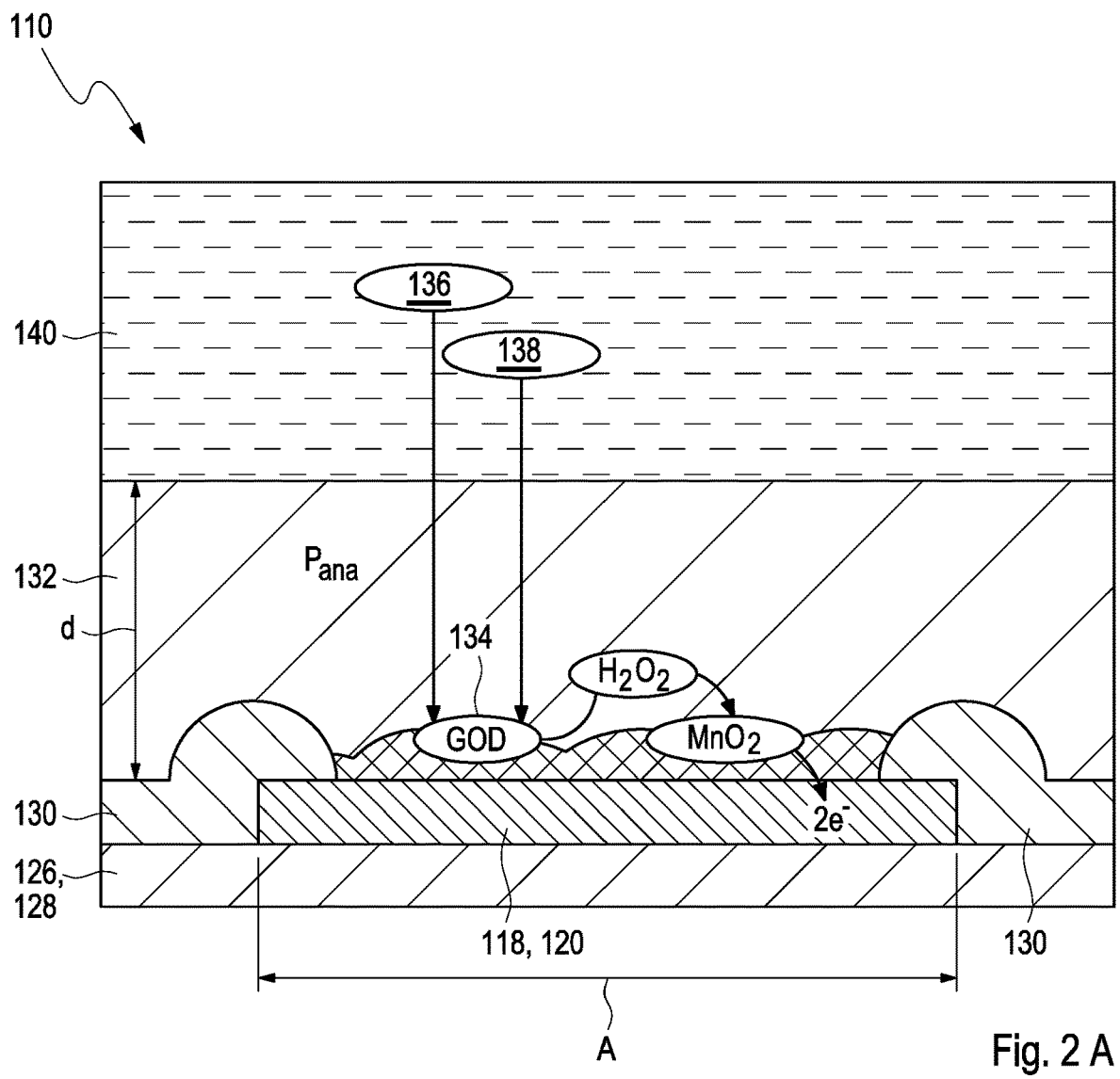
FIGS. 2A-2B illustrate schematic mechanisms for measuring a sensitivity of a biosensor (FIG. 2A) and for a dielectric characterization of a biosensor (FIG. 2B), respectively.
Figure 2:
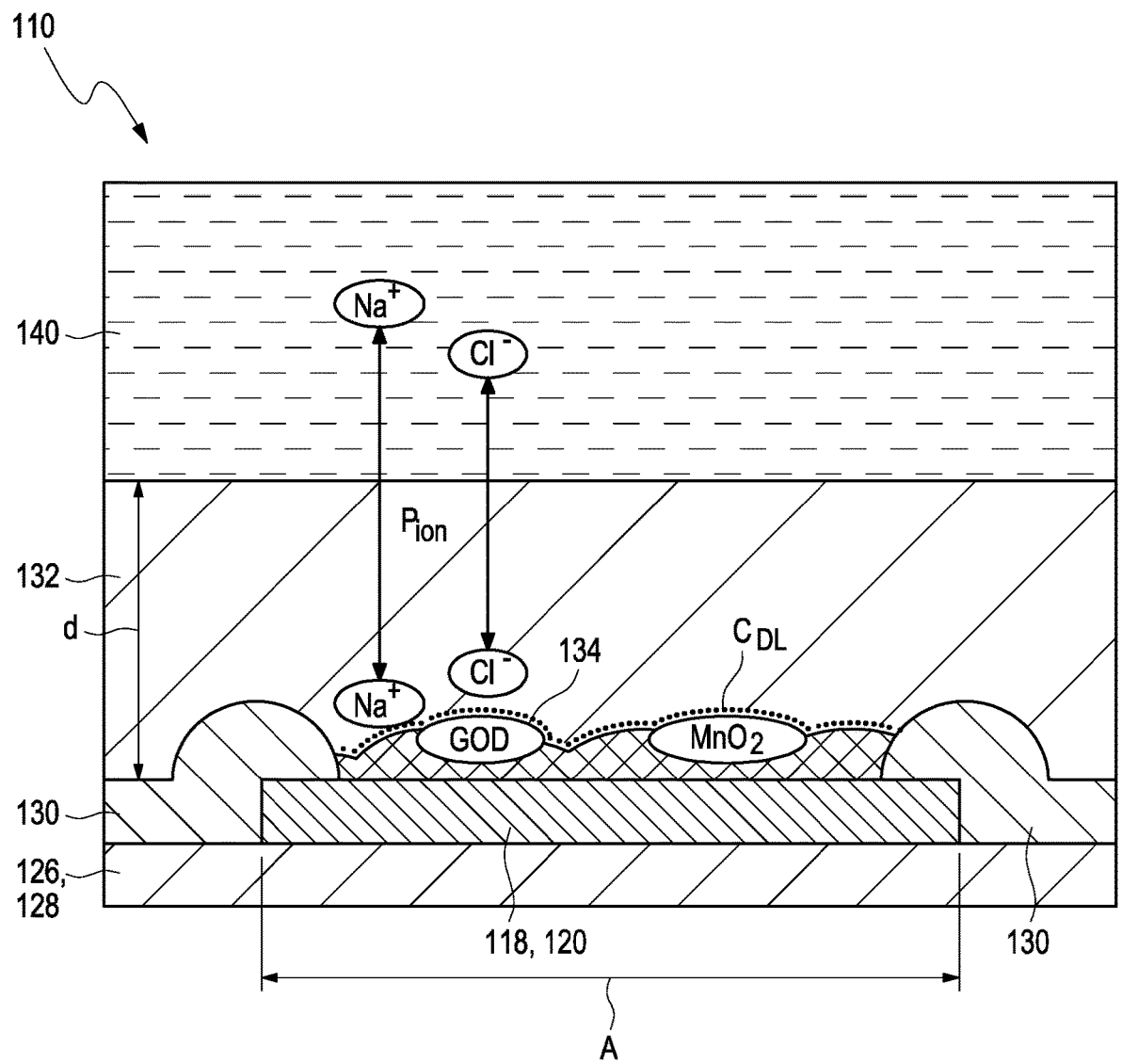

FIG. 2A illustrates, in a highly schematic manner, a particularly preferred mechanism of an in-vivo determination of the sensitivity S of the biosensor 110, which may also be referred to as a "functional testing" of the biosensor 110. In the biosensor 110, the working electrode 120 having a surface area A may, typically, be placed on a substrate 126, preferably on a flexible printed circuit board 128, and be furnished with solder resists 130. Further, the working electrode 120 is covered by a membrane 132 having a thickness d. Herein, the membrane 132 may, preferably, comprise an enzyme 134, in particular glucose oxidase, often abbreviated to "GOD." A reaction of an analyte 136, in particular glucose, and oxygen 138 as provided by the body fluid 140 may lead to a formation of hydrogen peroxide $H_2O_2$ which may react with manganese dioxide $MnO_2$ also being present at the surface of the working electrode 120 as catalyst and/or mediator, thereby providing free electrons 2 $e^-$ to the working electrode 120, whereby the direct raw current I is generated. According to Equation (3), $$S=P_{ana}/d \cdot A, \quad (3)$$

apart from the surface area A of the working electrode 120 and the thickness d of the membrane, a permeability $P_{ana}$ of the membrane 132 with respect to the analyte, such as glucose, may be capable of influencing the sensitivity S of the biosensor 110. As result, the functional testing of the biosensor 110 may provide the sensitivity S of the biosensor 110 which may depend from a number of variables, such as the thickness d and the area of the membrane 132 which may be varying due to manufacturing effects.

FIG. 2B illustrates in a highly schematic manner a particularly preferred mechanism of a measurement of an in-vivo current response indicative of an in-vivo admittance Y(t) of the biosensor 110, which may also be referred to as an in-vivo "dielectric characterization" or a "detection of in-vivo properties" of the biosensor 110. Again, the working electrode 120 of the biosensor 110 having the surface area A may, typically, be placed on the substrate 126, such as the flexible printed circuit board 128, and be furnished with solder resists 130. As particularly preferred, the working electrode 120 may be covered by the membrane 132 having a thickness d. Again, the membrane 132 may, preferably, comprise the enzyme 134, in particular glucose oxidase. According to Equation (4), $$Y(t)=\sim P_{ion}/d \cdot A, \quad (4)$$

the admittance Y(t) of the biosensor 110 may depend on a permeability $P_{ion}$ of the membrane with respect to the ions, such as $Na^+$ or $Cl^-$ ions, the thickness d of the membrane, and the area A of the electrode 118.

Figure 8:
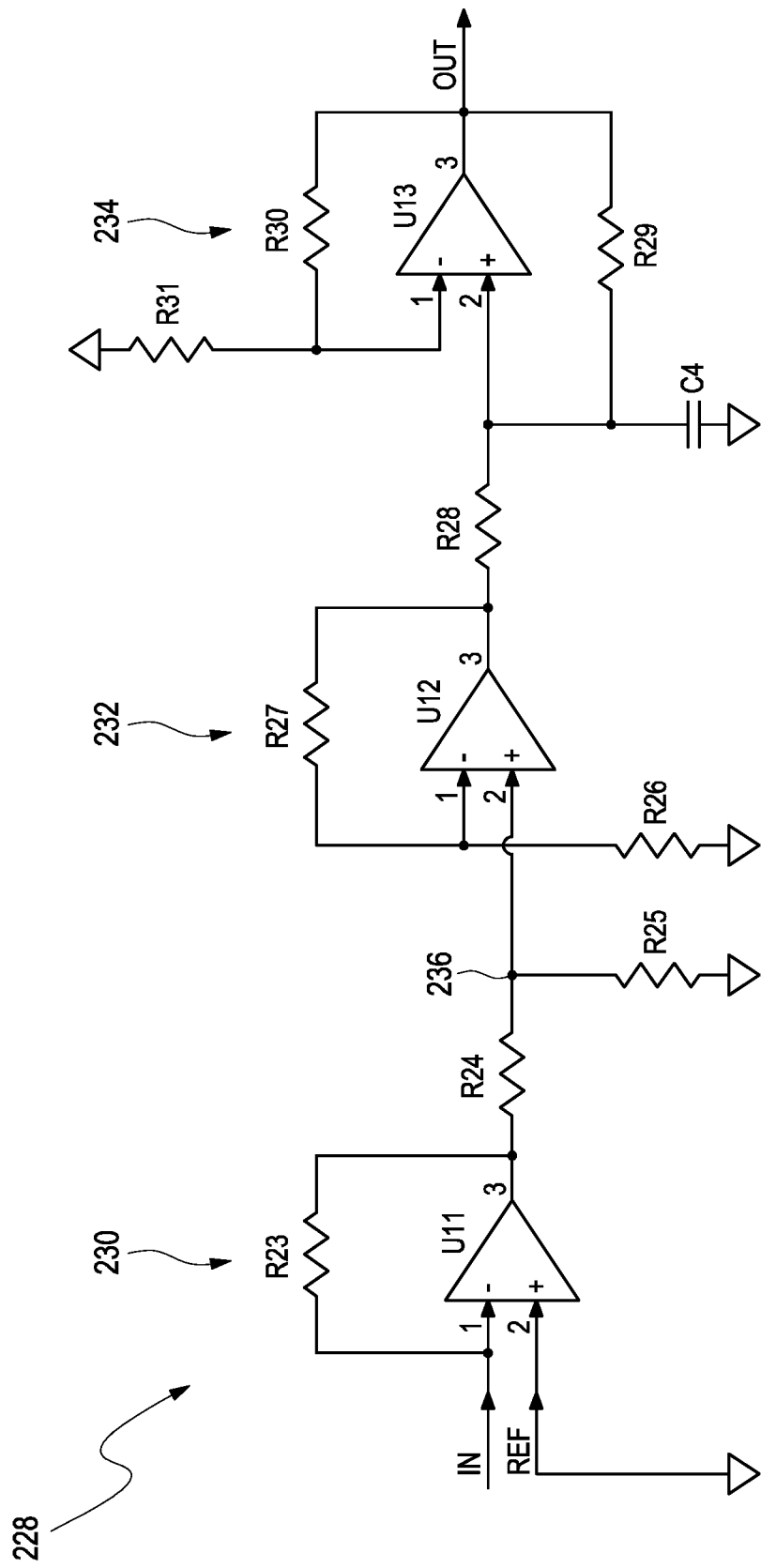
FIG. 8 illustrates a preferred example of a circuit especially adapted to charge determination.

As further indicated in FIG. 2B, the surface area A of the electrode 118 may be described by having a double layer being represented by a double-layer capacitance as schematically depicted in FIG. 8 below, wherein the double-layer capacitance may be determined by measuring the in-vivo current response of the biosensor 110. As used herein, the double-layer capacitance may be used as a quantity representing the surface area A of the electrode 118. A measurement of the double-layer capacitance may reveal changes related to electrode surface, in particular, loss of contact, draining, or detaching of the electrode 118. As a result, the measurement of the double-layer capacitance may be employed as additional parameter, particularly, adapted to provide additional failsafe information with regard to the operation of the biosensor.

By comparing the respective results as schematically illustrated in FIGS. 2A and 2B, a sensitivity-to-admittance ratio S(t)/Y(t) may be determined which, advantageously, only depends on a ratio of the respective membrane permeabilities $P_{ana}$, $P_{ion}$ with respect to the analyte and the ions in accordance with Equation (5):

$$S(t)/Y(t) = \sim P_{ana}/P_{ion} \tag{5}$$

As described above, the determined sensitivity-to-admittance ratio S(t)/Y(t) may allow providing information about a current state of the intrinsic membrane transport properties related to the respective permeabilities of the membrane 132 while the geometric properties of the biosensor, in particular the thickness d of the membrane 132 and the geometric area A of the working electrode 120, can be disregarded. As a result, by determining the sensitivity-to-admittance ratio S(t)/Y(t), a change of the thickness d of the membrane 132, such as by a swelling of the membrane 132 during an in-vivo operation of the biosensor 110, can be disregarded.

Figure 3:
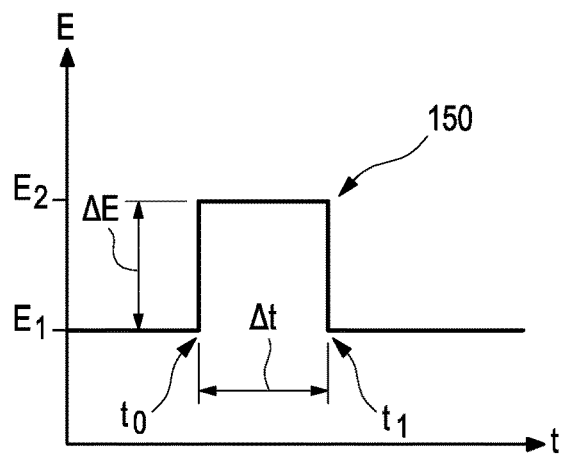
FIGS. 3A-3C illustrate an application of a potential step to the biosensor (FIG. 3A) and corresponding courses of a current response (FIG. 3B) and a related charge (FIG. 3C) of the biosensor.
Figure 3:
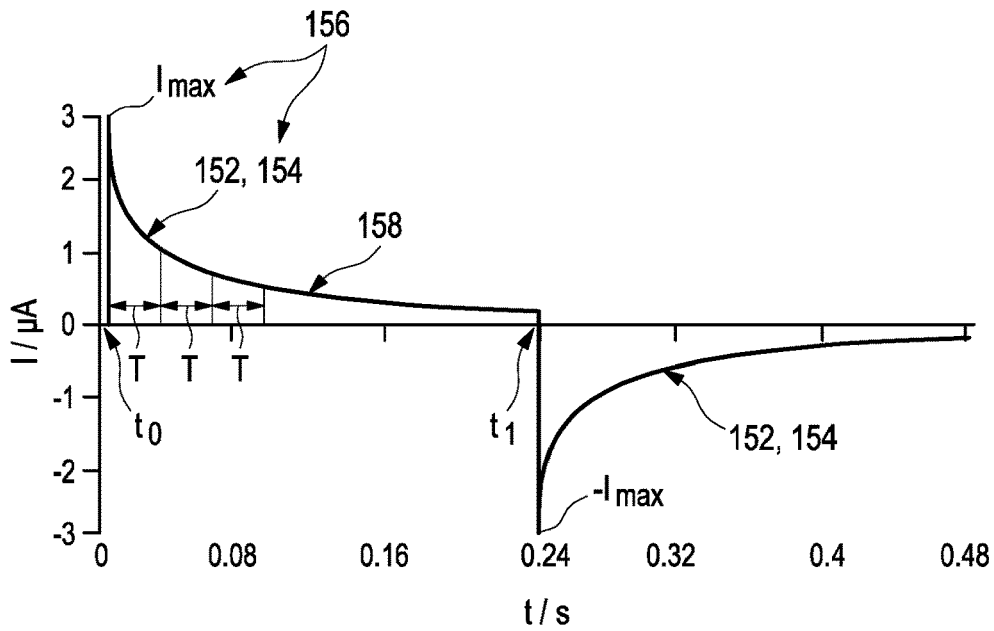
Figure 3:
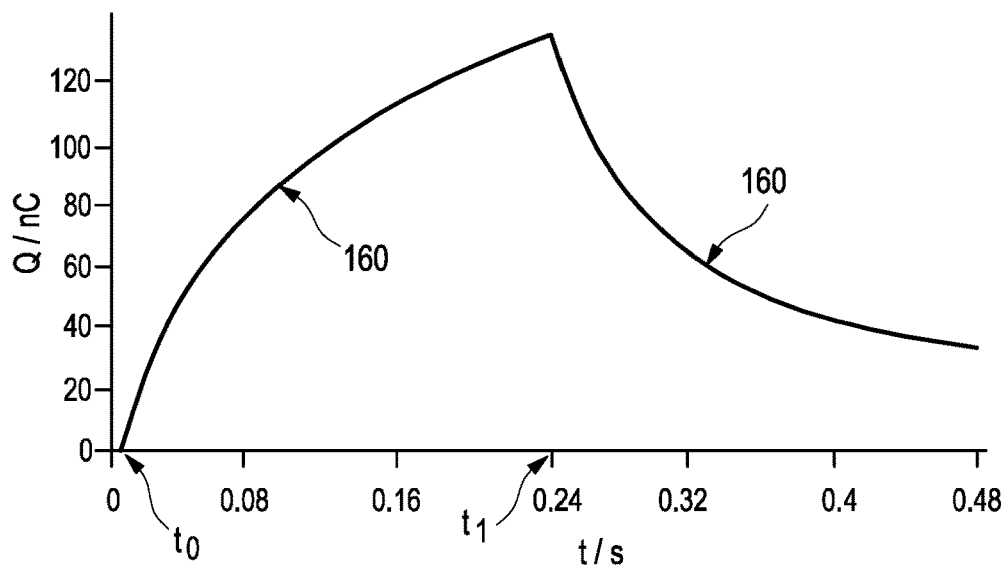

FIG. 3 illustrates an application of a potential step 150 to the biosensor 110 and a response of the biosensor 110 to the application of the potential step 150 as a preferred embodiment configured for determining the in-vivo current response indicative of the in-vivo admittance Y(t) of the biosensor.

As schematically depicted in FIG. 3A, the potential step 150 can be considered as the application of an enhanced electrical potential $E_2$ over a time interval $\Delta t = t_1 - t_0$ with respect to the electrical potential $E_1$ prevailing at the membrane, thus providing an electrical potential difference $\Delta E$ to the membrane over the time interval $\Delta t$. As an alternative (not depicted here), a diminished electrical potential $E_2$ may be applied over the time interval $\Delta t$ with respect to the electrical potential $E_1$ prevailing at the membrane, again, thus providing an electrical potential difference $\Delta E$ to the membrane over the time interval $\Delta t$. Further alternatives may use a different time-varying electrical potential, in particular, a time-varying waveform, at least one linear or non-linear sweep, or at least one cyclically varying signal, such as described above in more detail. For sake of simplicity, the potential step 150 will include any of these time-varying electrical potentials in the following.

FIG. 3B schematically shows a corresponding course 152 of a current response I(t) of the biosensor 110 as affected by a first application of a first potential step to the biosensor 110 at the time $t_0 = 0$ s and, subsequently, a second application of a second potential step to the biosensor 110 at the time $t_1 = 0.24$ s, whereby, in this particular example, the second application exhibits a reversed sign of the second potential step with respect to the first application of the first potential step. However, other kinds applications of potential steps are feasible, apart from varying the sign of the potential step 150 the height of the electrical potential difference $\Delta E$ may, alternatively or in addition, also be varied.

Taking hereby a capacitance C of the membrane 132 into consideration, the current I(t) at the membrane 132 after the application of the potential step 150 may, as schematically depicted in FIG. 3B, follow exhibit an exponential decay 154 which can, after the first application of the first potential step which exhibits a positive sign, be described by any one of Equations (6) or (7):

$$I(t) = \frac{E_2 - E_1}{R_M} e^{-\frac{t}{R_M \cdot C}} + \frac{E_2}{R_D} \tag{6}$$

or $$I(t) = I_{max} \cdot e^{-\frac{t}{\tau}} + I_0 \tag{7}$$

wherein $I_{max}$ denotes a maximum current and $I_0$ the zero current. For a negative sign of the potential step 150, the current I(t) at the membrane 132 after the second application of the second potential step can similarly be described with alternating signs.

As further indicated in FIG. 3B and Equation (8), the exponential decay 154 can be described by referring to a term $$\tau = R_M \cdot C, \tag{8}$$

wherein the term $\tau$ relates to a time constant $\tau$ which may be assigned to the exponential decay 154 of the current I(t) in consequence of the application of the potential step 150 to the biosensor 110. As generally used, the time constant $\tau$ may be defined as relating to a time interval after which an initial intensity at the beginning of the time interval has decreased to a value of approximately $1/e \approx 0.367879$ of the initial intensity. However, other kinds of definitions for the time constant $\tau$ may also be applicable, such as a decay of the intensity after the time interval to a value of approximately ½ of the initial intensity.

In particular, the exponential decay 154 as schematically depicted in FIG. 3B may, thus, be used for determining the electrical resistance $R_M$ of the membrane 132 according to Equation (9)

$$R_M = \Delta E / I_{max}, \tag{9}$$

whereby only the height of the electrical potential difference $\Delta E$ as applied to the biosensor 110 during the potential step 150 and the observed maximum current $I_{max}$ which can be derived from the course 152 of a current response I(t) of the biosensor 110 at the first operating point 156 below the time constant $\tau$, preferably at a time interval of 10 μs to 100 μs after the application of the potential step 150.

As further schematically depicted in FIG. 3B, a second operating point 158 is, in addition, selected above $\tau$, preferably above $2\tau$, $3\tau$, $4\tau$, or $5\tau$, for determining the electrical capacity C of the working electrode 120. By applying the general definition of the capacitance C according to Equation (11)

$$C = Q/\Delta E, \tag{11}$$

this may allow determining the additional charge $$Q(t) = \int I(t) dt, \tag{12}$$

which has been provided to the membrane 132 by application of the potential step 150.

FIG. 3C schematically depicts a corresponding course 160 of the additional charge Q(t) of the biosensor 110 as affected by the first application of the first potential step to the biosensor 110 at the time $t_0 = 0$ s and, subsequently, the second application of the second potential step to the biosensor 110 at the time $t_1 = 0.24$ s, whereby, in this particular example, the second application, again, exhibits the reversed sign of the second potential step with respect to the first application of the first potential step.

Figure 4:
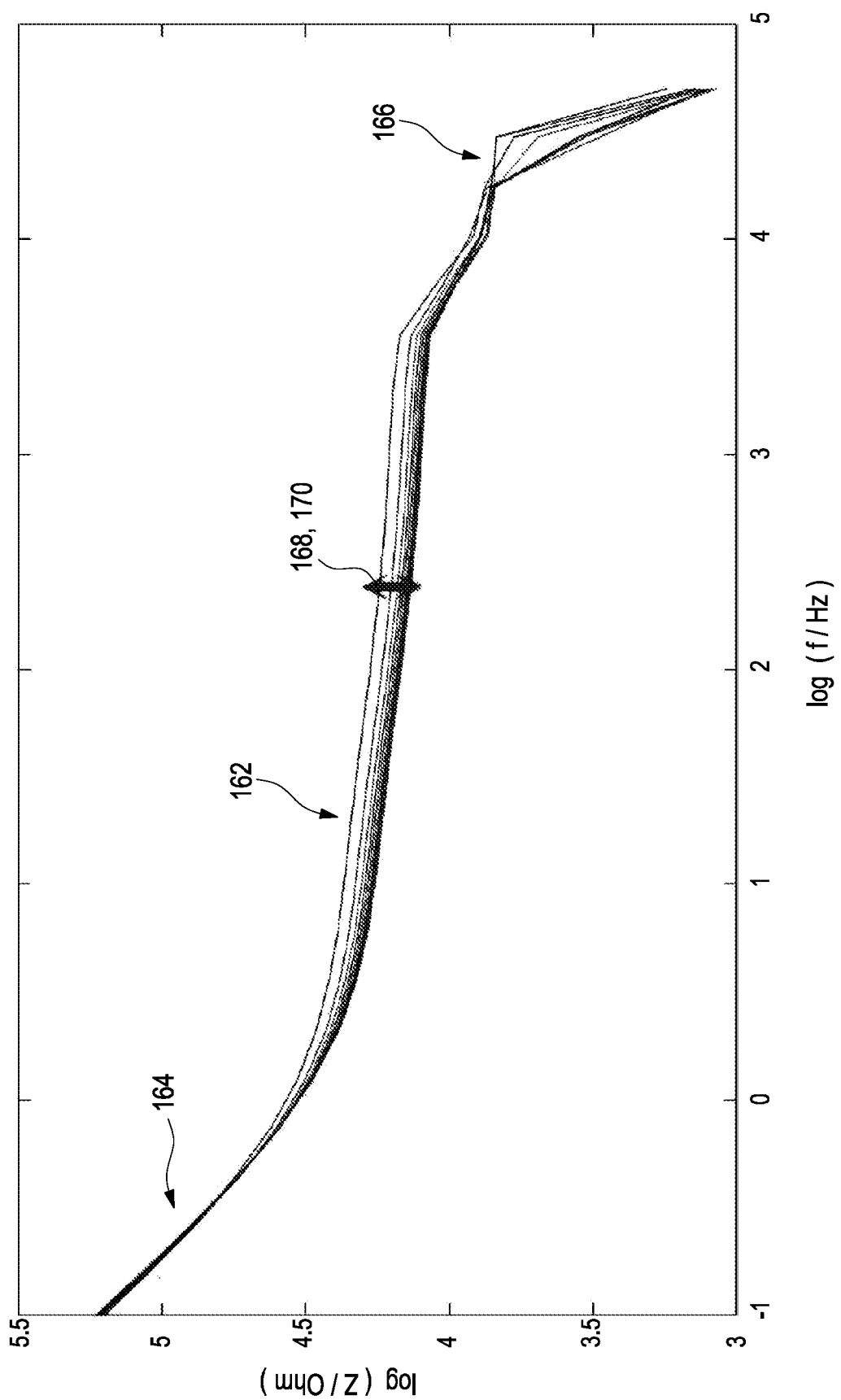
FIG. 4 illustrates a depiction of a corresponding course of the impedance of the biosensor in a Bode plot visualizing a frequency behavior of the biosensor.

FIG. 4 schematically depicts a "Bode plot" which, usually, describes a combination of a Bode magnitude plot referring to intensity versus an applied frequency $f$ and a Bode phase plot referring to a phase shift versus the applied frequency $f$. As shown in FIG. 4 on the left-hand side, a logarithm of the absolute value of the impedance Z in Ohm and, on the right-hand side, a phase shift of the response of the biosensor 110 is plotted versus the logarithm of the frequency $f$ with respect to the base 10 of the alternating electric voltage or current as applied to biosensor 110. In FIG. 4, various curves 162 refer to the Bode magnitude plot related to the logarithm of the absolute value of the impedance Z versus the logarithm of the frequency $f$.

As can be further seen in FIG. 4, the curves 162 exhibit various features which may occur at predefined frequency ranges. On one hand, an increase 164 of the impedance Z observable towards lower frequencies is, usually, considered to be attributable to a capacitive behavior of the double layer $C_{DL}$ as described above with reference to FIG. 2B. On the other hand, a decrease 166 of the impedance Z observable towards higher frequencies is, usually, considered to be attributable to a high-frequency Ohmic behavior of the membrane resistance.

As further disclosed by FIG. 4, the curves 162 exhibit a distinction 168 with respect to each other, particularly, in a range of 1 Hz to 10 kHz, in particular of 3 Hz to 3 kHz, especially of 10 Hz to 1 kHz. This behavior which expresses an alteration 170 of the electrical resistance of the membrane 132 can, generally, be attributed to an alteration of the permeability and thickness of the membrane 132, such as in consequence of a swelling of the membrane 132 during the in-vivo operation of the biosensor 110 as described above. Thus, it may be particularly be advantageous to measure the impedance Z of the biosensor 110 by application of a single frequency in the indicated range.

Figure 5:
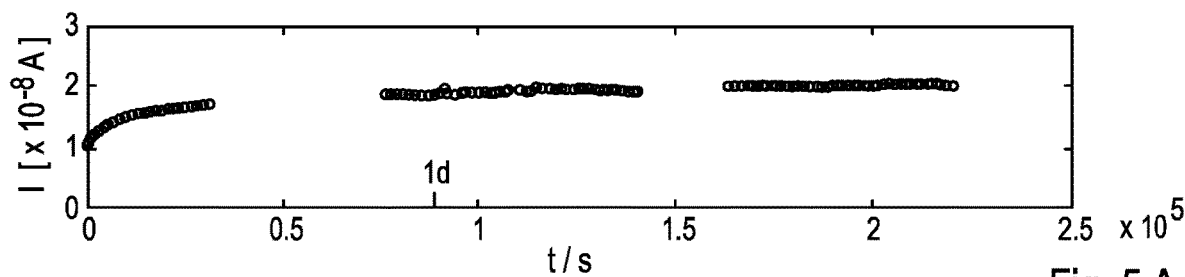
FIGS. 5A-5E illustrate a temporal course of a sensitivity (FIG. 5A), of an admittance (FIG. 5B), of a sensitivity-to-admittance ratio (FIG. 5C), of a relative deviation of the sensitivity-to-admittance ratio from a median (FIG. 5D), and of a capacitance (FIG. 5E) of the biosensor.
Figure 5:
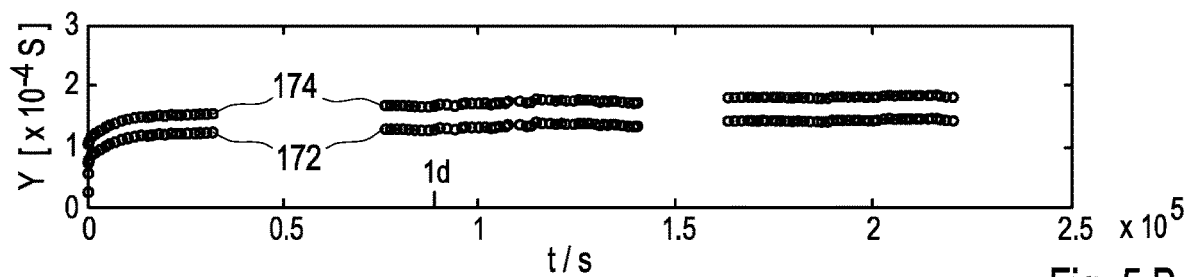
Figure 5:
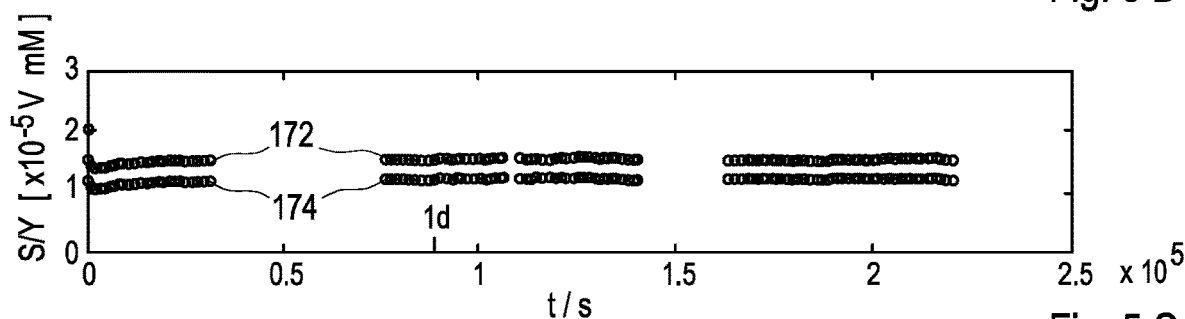
Figure 5:
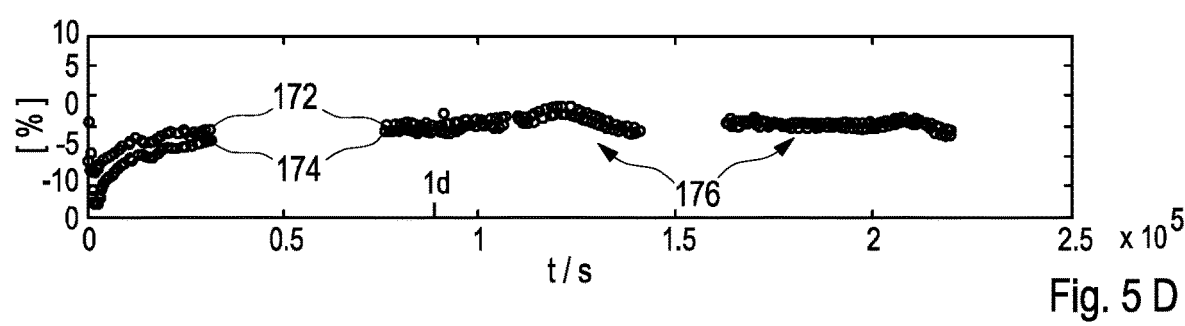
Figure 5:
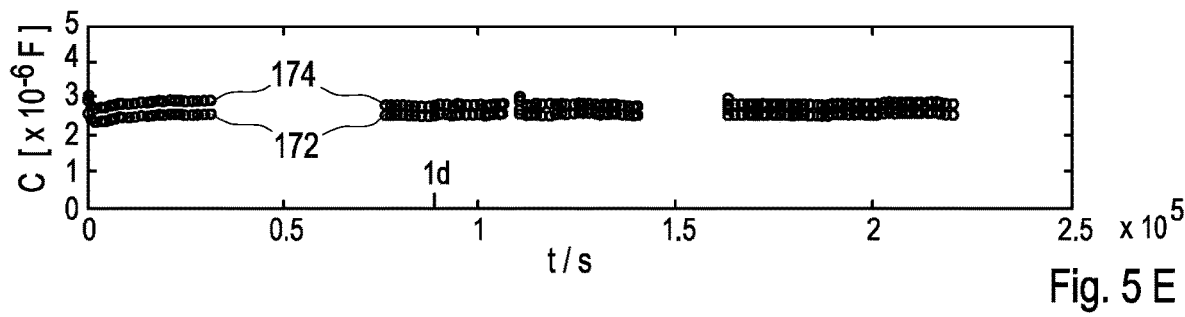

FIG. 5 illustrates temporal courses of a number of quantities related to the biosensor 110 which may be provided by the measurements as described herein.

Firstly, FIG. 5A illustrates the temporal course of the current response I(t) of the biosensor 110 at a constant concentration c of the analyte which is, according to Equation (1), proportional to the sensitivity S of the biosensor 110. As can be derived from FIG. 5A, a large sensitivity change accumulating up to 100% may occur, in particular, due to a swelling of the membrane 132 as, for example, expressed by Equation (3). As a result, the sensitivity S of the biosensor 110 is receptive to the operation of the biosensor 110 and, thus, not suited for determining an in-vivo drift in the biosensor 110 even when the concentration c of the analyte may stay constant.

Similarly, FIG. 5B illustrates temporal courses of the admittance Y(t) of the biosensor 110, wherein curve 172 was obtained by application of a potential step 150 while curve 174 was obtained by application of electrochemical impedance spectroscopy (EIS), in particular for purposes of comparison. Irrespective of a manner of generation of the curves 172, 174, the admittance Y of the biosensor 110 depends on the geometric properties of the biosensor 110 since it changes its value due to the swelling of the membrane 132 as, for example, expressed by Equation (4).

In contrast hereto, FIG. 5C illustrates temporal courses of the sensitivity-to-admittance ratio S(t)/Y(t) of the biosensor 110, which, according to Equation (5), do not depend on the geometric properties of the biosensor, in particular neither on the thickness d of the membrane 132 nor on the surface area A of the working electrode 120. Again, curve 172 was obtained by application of a potential step 150 while curve 174 was obtained by application of EIS. As a result, the sensitivity-to-admittance ratio S(t)/Y(t) of the biosensor 110 allows providing information about a current state of the intrinsic membrane transport properties related to the permeabilities $P_{ana}$, $P_{ion}$ of the membrane 132 with respect to the analyte and to the ions. As can be derived from FIG. 5C, as long as the intrinsic membrane transport properties stays constant, the temporal course of the sensitivity-to-admittance ratio S(t)/Y(t) of the biosensor 110 remains unaffected by other changes of the membrane 132, such as the swelling of the membrane 132 over the time interval as depicted here. Consequently, the sensitivity-to-admittance ratio S(t)/Y(t) of the biosensor 110 as depicted in FIG. 5C, thus, allows determining the in-vivo drift of the biosensor 110 which is, subsequently, compensated when determining the analyte value by using the raw current.

As a kind of enlargement of FIG. 5C, FIG. 5D illustrates temporal courses of a relative deviation of the sensitivity-to-admittance S(t)/Y(t) ratio from a median given in percent of the deviation from the median, wherein, again, curve 172 was obtained by application of a potential step 150 while curve 174 was obtained by application of EIS. As can be derived from FIG. 5D, the relative deviation of the sensitivity-to-admittance S(t)/Y(t) ratio from the median remains constant over the depicted time interval apart from time periods 176 in which the temperature of the membrane 132 in the biosensor 110 slightly varies. In fact, the variations of the temperature can be considered particularly small since they are too small to attract attention in FIG. 5C. This kind of behavior, thus, clearly demonstrates that the determination of the sensitivity-to-admittance S(t)/Y(t) ratio appears a reasonable quantity particularly suited for determining the in-vivo drift of the biosensor 110 since a temperature change may be considered as a factor triggering an in-vivo drift of the biosensor 110.

As an alternative measure, FIG. 5E illustrates temporal courses of the capacitance C of the biosensor 110, again, showing curve 172 which was obtained by application of a potential step 150 while curve 174 was obtained by application of EIS. Similar to FIG. 5C, the temporal course of the capacitance C of the biosensor 110 stays practically constant over the depicted time interval.

Figure 6:
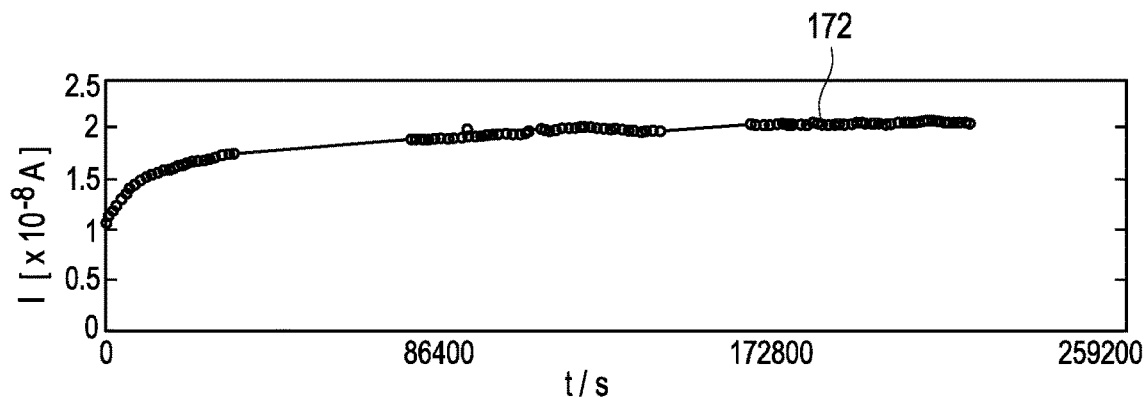
FIGS. 6A-6C illustrate a temporal course of the current (FIG. 6A), the admittance (FIG. 6B), and of a current-to-admittance ratio (FIG. 6C) in a biosensor.
Figure 6:
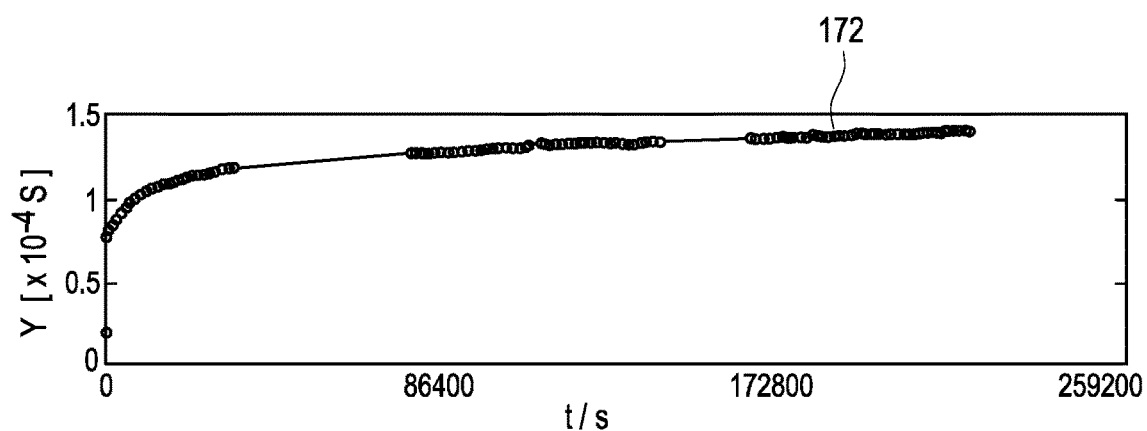
Figure 6:
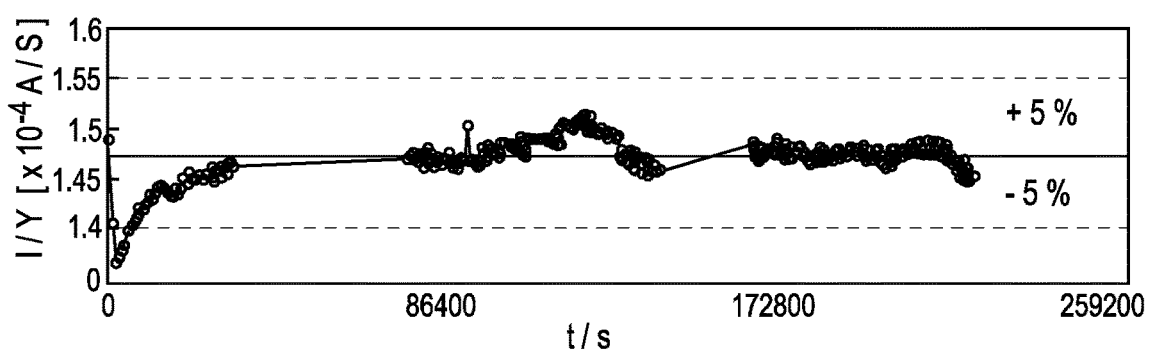

FIG. 6 presents a further example of temporal courses of a number of in-vivo properties related to the biosensor 110 which may be provided by the application of a potential step 150 s described herein, wherein, in contrast to FIGS. 5A to 5E, the time scale extends here over more than two and a half complete days.

Herein, FIG. 6A illustrates the temporal course of the current response I(t) of the biosensor 110 at constant concentration c=10 mM of the analyte glucose. The corresponding admittance Y(t) of the biosensor 110 is depicted in FIG. 6B while a corresponding current-to-admittance ratio I(t)/Y(t) as shown in FIG. 6C is proportional to the sensitivity-to-admittance S(t)/Y(t) ratio of the biosensor 110 at a constant concentration of the analyte as applicable here. Again, from FIG. 6C it may be derived that, apart from the first hours of operation, the sensitivity-to-admittance S(t)/Y(t) ratio of the biosensor 110 remains constant within thresholds of ±5%, thus, implying here a perfectly compensated sensitivity drift of the biosensor 110.

Figure 7:
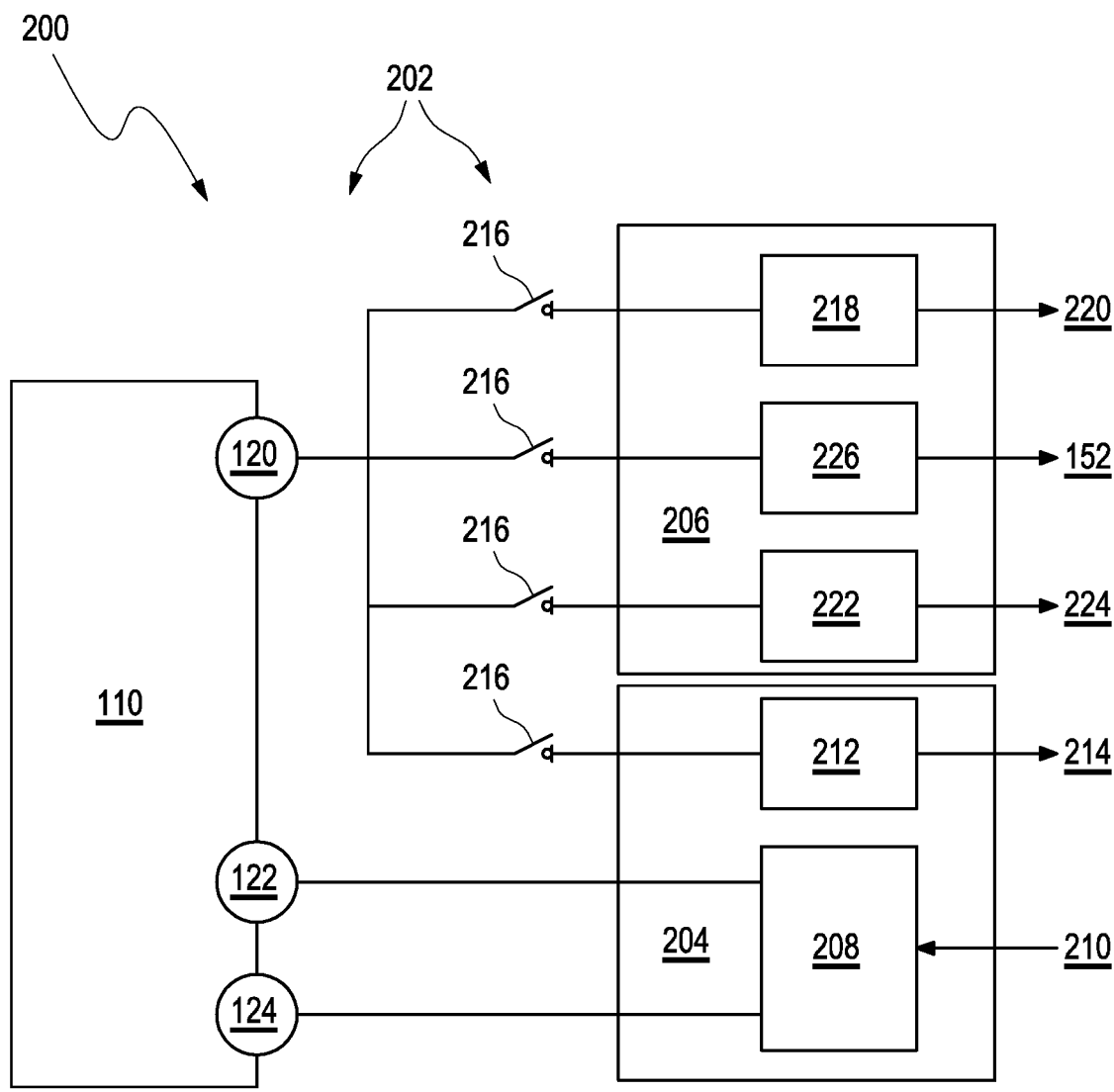
FIG. 7 illustrates a schematic circuit diagram of the system comprising a biosensor and an electronics device.

FIG. 7 illustrates a schematic circuit diagram of the system 200 comprising the biosensor 110 and an electronics unit 202, wherein the electronics unit 202 comprises a direct current measuring unit 204 and a potential step response measuring unit 206. Compared to other possible embodiments, the circuit of FIG. 7 comprises more analogue electronic elements which allow reducing the load on microcontrollers, thus, providing a faster processing within the electronics unit 202 with reduced technical effort.

As depicted in FIG. 7, the direct current measuring unit 204 comprises an analog controller 208, which may control the potentiostat 114 as described above, which may be driven by an input 210, and which drives the electrodes 118, in particular the working electrode 120, the reference electrode 122, and the counter electrode 124, in particular by application of an electrical potential in order to measure the raw current I and, in addition, of the potential step 150 for measuring the in-vivo admittance the biosensor 110. Further, the direct current measuring unit 204 comprises a glucose current measuring unit 212, which is adapted to measure and to provide a DC output 214, which is the raw current I or a value related to the raw current I, preferably, a voltage converted raw current I, as measured for the analyte glucose. However, other kinds of values may also be provided at the DC output 214.

As further shown in the exemplary embodiment of FIG. 7, the electronics unit 202 further comprises a number of switches 216 (four switches 216 are actually depicted here) which are configured to allow switching an output of the biosensor 110, in particular of the working electrode 120, between the glucose current measuring unit 212 as comprised by the direct current measuring unit 204 and one or more units as comprised by the potential step response measuring unit 206, in particular, to allow measuring the admittance of the biosensor 110 in addition to the raw current I.

For this purpose, the potential step response measuring unit 206 may comprise a charge counter 218 which may provide a value related to the charge C accumulated in the membrane 132 of the working electrode 120 to a charge output 220. A preferred example of a circuit configured to be used as the charge counter 218 is shown in FIG. 8.

Further, the potential step response measuring unit 206 may comprise a peak detector 222 which may provide information related to a peak the charge accumulated in the membrane 132 of the working electrode 120 to a peak information output 224, wherein the peak information may, preferably, be the maximum current $I_{max}$ or a value related hereto, in particular, a voltage converted maximum current $I_{max}$. Three different exemplary embodiments of a circuit configured to be used as the peak detector 222 are shown in FIGS. 9A to 9C.

According to the exemplary embodiment as depicted in FIG. 7, the potential step response measuring unit 206 may, in addition, comprise a fast sampling block 226, which may be configured to allow a fast sampling of the course 152 of the current response I(t) to the application of the potential step 150 to the biosensor 110. Herein, the course 152 of the current response I(t) may, thus, provide additional information that can be used in addition to the charge C and the maximum current $I_{max}$ as provided by the other two units 218, 222 of the potential step response measuring unit 206. In addition hereto, the potential step response measuring unit 206 may comprise further units for processing outputs as provided by the biosensor 110 and, hereby, acquiring additional information or the same information, in particular, for a purpose of redundancy.

As mentioned above, FIG. 8 shows a preferred example of a circuit 228 for charge determination. As illustrated there, the circuit 228 comprises three successive stages 230, 232, 234, wherein each stage 230, 232, 234 has an operational amplifier. Herein, the first stage 230 is a current-voltage converter which provides the voltage-conversed course 152 of the current response I(t) at a connection point 236 after a resistor R24 as output. The second stage 232 is a differential amplifier while the third stage 234 is an integration unit which is configured to provide the desired value for the charge C at the output of the circuit 228.

Figure 9:
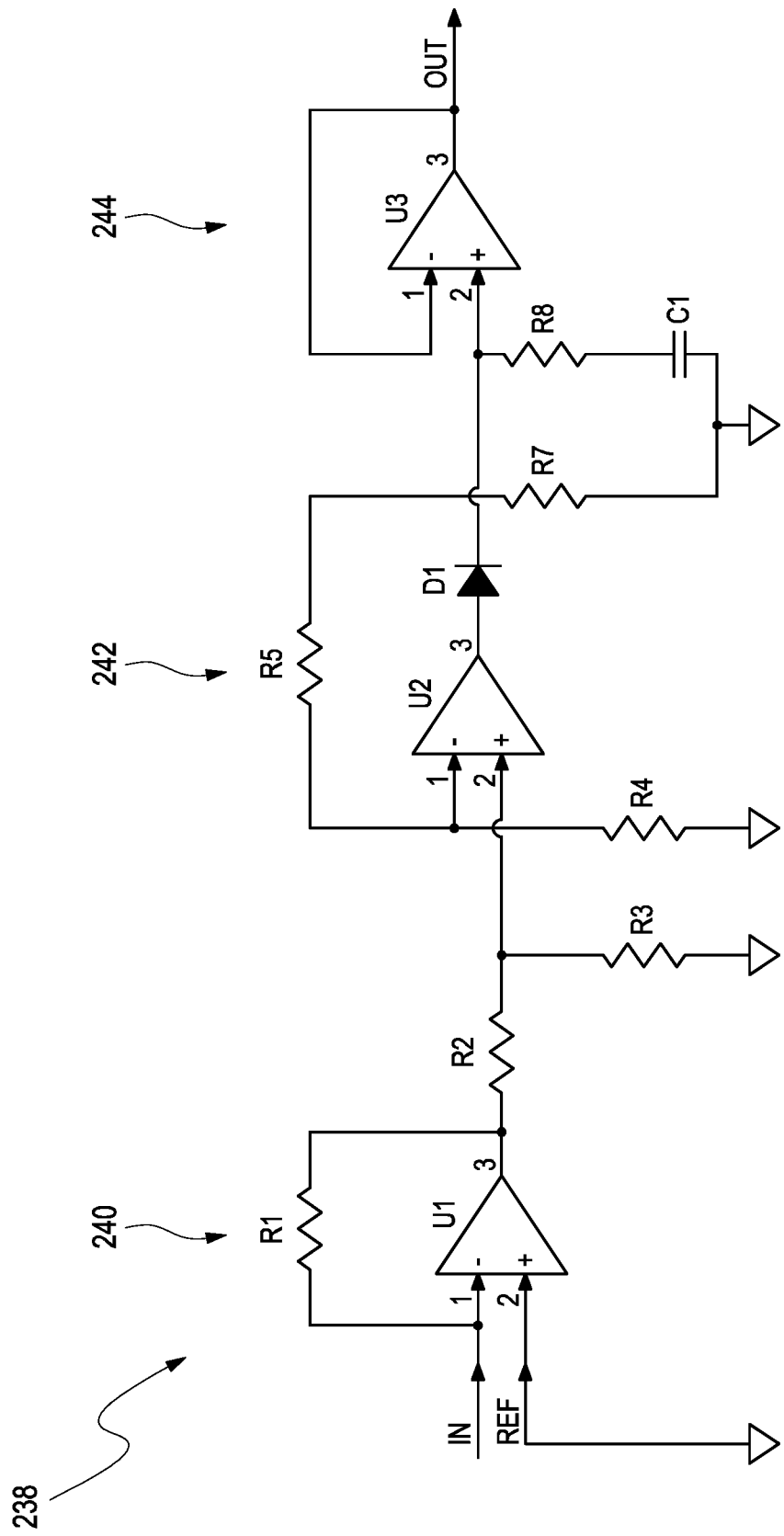
FIGS. 9A-9C illustrate three preferred examples of circuits especially adapted to peak determination.
Figure 9:
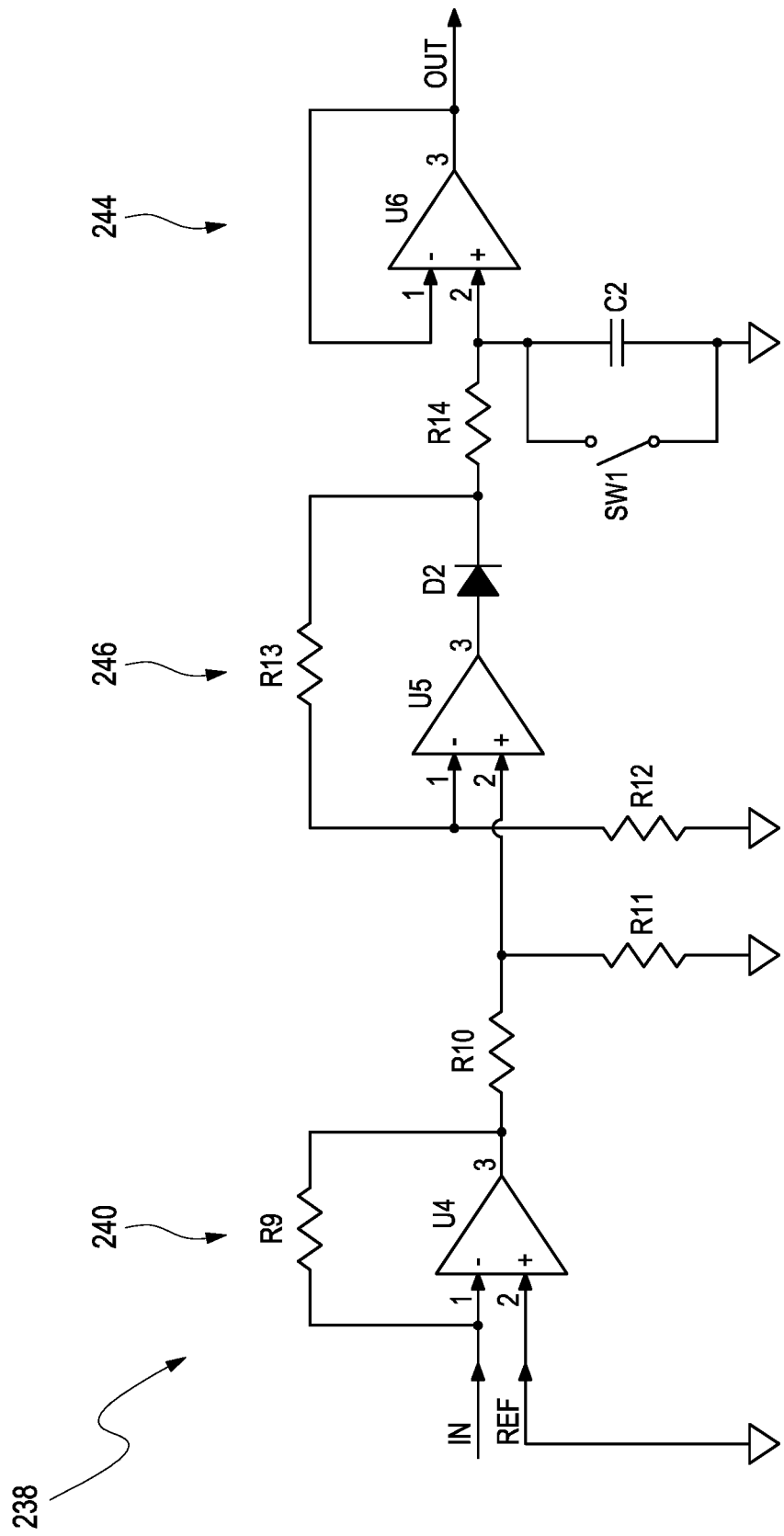
Figure 9C:
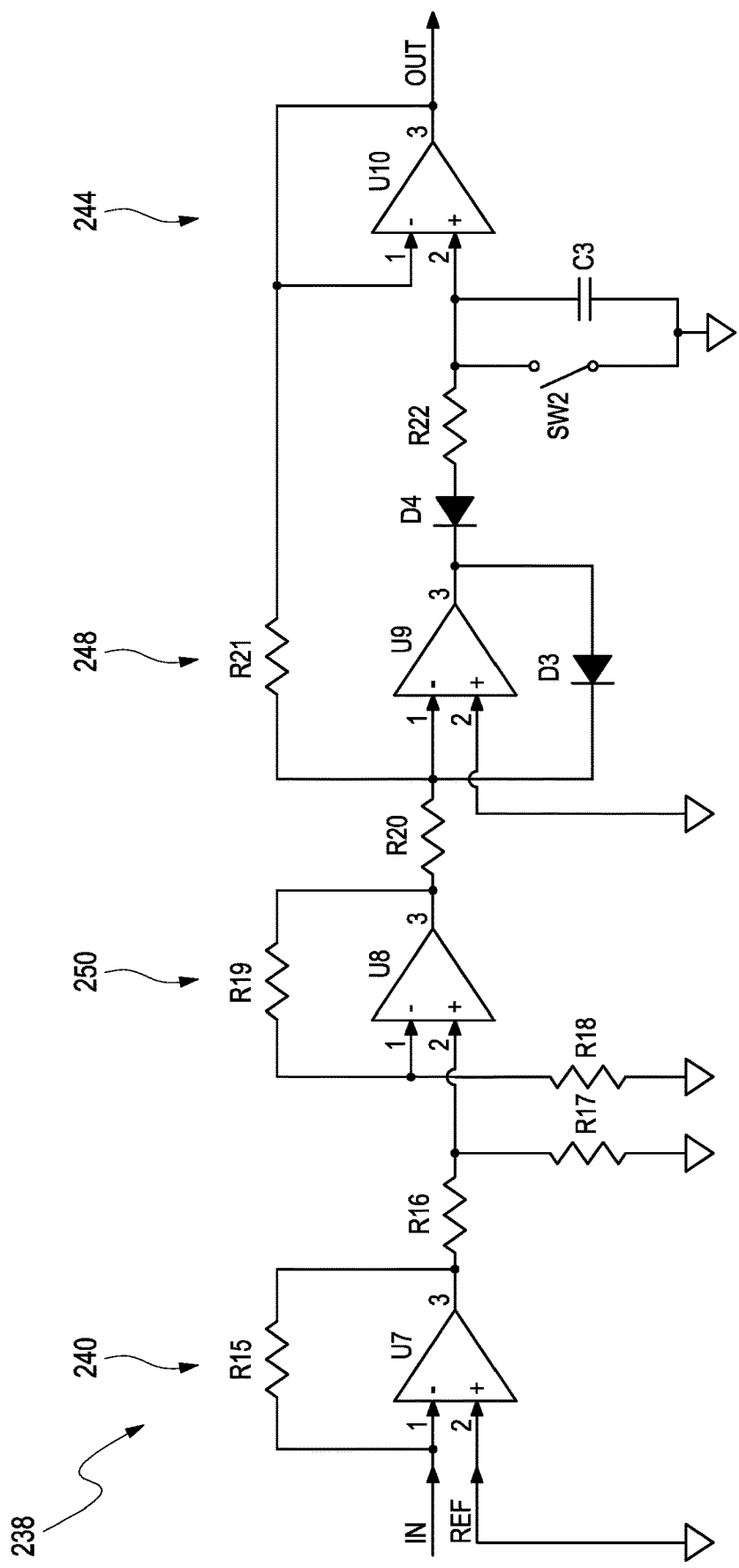

FIGS. 9A to 9C each illustrate a preferred example of a circuit 238 which is especially adapted to peak determination.

As shown in FIG. 9A, the circuit 238 comprises three successive stages 240, 242, 244, wherein each stage 240, 242, 244 has an operational amplifier. Herein, the first stage 240 is, again, a current-voltage converter while the third stage 244 is, again, a differential amplifier. The second stage 242 comprises a combination of a capacitor C1 and a reverse-biased diode D1 which provide that incoming charges are stored in the capacitor C1 which cannot immediately be discharged due to the reverse-biased diode D1. As a result, a peak value can be determined by the combination of the capacitor C1 and the reverse-biased diode D1 which is, subsequently, be amplified in the third stage 244. An eventual discharge of the capacitor C1 can, according to this particular embodiment, only be achieved after a period of time. Only after this period of time a further peak value may be determined by using this particular embodiment of the circuit 238.

Thus, in order to allow a faster repetition of measurements, the amended circuits 238 for peak determination as shown in FIGS. 9B and 9C may, preferably be used. Herein, the circuit 238 of FIG. 9B comprises a second stage 246 which has a combination of a diode D2, a capacitor C2 and a switch SW1, wherein the switch SW1 may be used for discharging the capacitor D2 if required. Further, the circuit 238 of FIG. 9C comprises an arrangement having four stages 240, 250, 248, 244 which allows an improved peak determination.

As mentioned above, the present method further comprises monitoring a failsafe operation of the biosensor 110. For this purpose, a combination of at least two, preferably three measured values may be used. In particular, the following values may be considered to be related to corresponding technical parts and effects:

the sensitivity S of the biosensor 110 may be related to an activity of the enzyme in the membrane 132, to an amount of catalyst and/or mediator in the membrane 132, and to a calibration value, particularly acquired by factory calibration or by initial calibration;

the electrical resistance $R_M$ of the membrane 132 may, on one hand, be related to a swelling of the membrane 132 in-vivo (leading to a slow reaction when swelling) and, on the other hand, to a contact of the membrane 132 with the electrode material (leading to a fast reaction in case of loss); and the electrical capacitance C of the working electrode 120 may, on one hand, be related to an amount of catalyst and/or mediator at the working electrode 120 (leading to a slow reaction in case of loss) and, on the other hand, to a loss of contact of the working electrode 120 with the electrode pad (leading to a fast reaction in case of loss).

Consequently, information concerning a behavior the sensitivity S of the biosensor 110 may be insufficient since they may be due to a number of different alterations within the biosensor 110. However, by combining the information concerning the behavior of the sensitivity S of the biosensor 110 with further information about the electrical resistance $R_M$ of the membrane 132 and the electrical capacitance C of the working electrode 120 may, nevertheless be capable for monitoring the failsafe operation of the biosensor 110, in particular, in accordance with the following Table. Herein, an availability of the sensitivity S of the biosensor 110 by in-vivo calibration may determine whether the information about the electrical resistance $R_M$ of the membrane 132 and the electrical capacitance C of the working electrode 120 can be used for compensation or as in a failsafe operation.

As indicated in the Table, a possible reaction with regard to observations of change in at least one of the sensitivity S of the biosensor 110, the electrical resistance $R_M$ of the membrane 132, and the electrical capacitance C of the working electrode 120 may be selected from at least one of:

an automatic "sensitivity-drift compensation;"
an indication of a "no valid value;"
a recommendation for "recalibration;" or
a request for "shut-off" of the biosensor 110.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

134 enzyme
136 analyte
138 oxygen
140 body fluid
150 potential step
152 course of current response I(t)
154 exponential decay
156 first operating point
158 second operating point
160 course of additional charge $Q(t)$
162 curves in a Bode phase plot
164 increase towards lower frequencies
166 decrease towards higher frequencies
168 distinction
170 alteration of the electrical resistance
172 curve obtained by application of potential step
174 curve obtained by application of alternating current
200 system
202 electronics unit
204 direct current measuring unit
206 potential step response measuring unit
208 analog controller
210 input
212 glucose current measuring unit
214 DC output

| Cause | Occurrence | S | R | C | Possible reaction |
|---|---|---|---|---|---|
| positive sensitivity drift due to membrane swelling | beginning to mid of wear-time | + (due to increased permeability of membrane for glucose) | − (due to increased permeability of membrane for ions) | o (no change) | none OR sensitivity-drift compensation |
| negative sensitivity drift due to encapsulation of membrane | mid to end of wear time | − (due to reduced mass transport to sensor due to encapsulation) | + (due to a reduced current path for ion conduction due to encapsulation) | o (no change) | sensitivity-drift compensation OR no valid value OR recalibration |
| sudden membrane defect | any time during wear time | ++ (due to far better mass transport of glucose to enzyme) | −− (due to far better ion conductivity as a result of defect) | o (no change) | no valid value OR recalibration OR shut-off |
| sudden loss of contact between paste electrode and pad | any time during wear time | −− (due to less active and/or less contacted area) | o/+ (depending on electrode setup, constant OR sudden increase) | −− (due to sudden decrease in area and/or mediator and/or catalyst) | no valid value OR recalibration OR shut-off |
| slow loss of catalyst and/or mediator | any time during wear time | − (after previous reduction in C; due to less catalyst and/or mediator) | o (constant) | −− (due to slow loss of mediator and/or catalyst) | no valid value OR recalibration OR shut-off |
| slow loss of enzyme activity | mid to end of wear time | − (slow loss due to decrease in enzyme activity) | o (constant) | o (constant) | no valid value OR recalibration OR shut-off |

LIST OF REFERENCE NUMBERS 110 biosensor
112 electrical circuit
114 potentiostat
116 output
118 electrode
120 working electrode
122 reference electrode
124 counter electrode
126 substrate
128 printed circuit board
130 solder resist
132 membrane
216 switches
218 charge counter
220 charge output
222 peak detector
224 peak information output
226 fast sampling block
228 circuit for charge determination
230 stage
232 stage
234 stage
236 connection point
238 circuit for peak determination
240 stage
242 stage 244 stage
246 stage
248 stage
250 stage

What is claimed is:

1. A method for detecting in-vivo properties of a biosensor adapted for determining a value of an analyte in a body fluid sample, the biosensor having a working electrode covered by a membrane and an enzyme for providing a reaction with the analyte, the method comprising:
   a) providing a sensitivity-to-admittance relation of the biosensor;
   b) measuring a raw current in the biosensor;
   c) measuring an in-vivo current response indicative of the in-vivo admittance of the biosensor, wherein the in-vivo current response is measured at first and second operating points and a time constant $\tau$ is determined by the electrical capacitance C of the working electrode and the electrical resistance $R_M$ of the membrane by $\tau=R_M C$, wherein the first operating point is selected below $\tau$ and the second operating point is selected above $\tau$;
   d) determining an analyte value in a sample of a body fluid by using the raw current and compensating an in-vivo sensitivity drift in the biosensor, wherein the in-vivo sensitivity drift is compensated by using the measured value for the raw current and a corrected value for the sensitivity, whereby the sensitivity is determined by using the sensitivity-to-admittance relation from step a); and
   e) monitoring a failsafe operation of the biosensor by using the in-vivo current response measured at the first and second operating points.

2. The method according to claim 1, wherein the first operating point is selected for providing a first characteristic value related to the electrical resistance of the membrane and wherein the second operating point is selected for providing a second characteristic value related to the electrical capacitance of the working electrode.

3. The method according to claim 2, wherein the in-vivo current response of the biosensor is determined by applying a potential step to an electrical potential difference at the biosensor, wherein the potential step comprises applying an additional electrical potential between the working electrode and a reference electrode of the biosensor over a time interval.

4. The method according to claim 1, wherein the second operating point is selected above $3\tau$.

5. The method according to claim 4, wherein the second operating point is selected above $5\tau$.

6. The method according to claim 1, wherein the failsafe operation of the biosensor is monitored by using at least one of (i) the sensitivity determined from the sensitivity-to-admittance relation of the biosensor, (ii) the electrical capacitance C of the working electrode, and (iii) the electrical resistance $R_M$ of the membrane.

7. The method according to claim 6, wherein a structural modification of the biosensor is determined by monitoring alterations of at least two of (i) the sensitivity determined from the sensitivity-to-admittance relation, (ii) the electrical capacitance C of the working electrode, and (iii) the electrical resistance $R_M$ of the membrane.

8. The method according to claim 1, wherein the sensitivity-to-admittance relation is obtained during a calibration of the biosensor, wherein the calibration of the biosensor is selected from at least one of a multiple calibration, an initial calibration, and a factory calibration.

9. The method according to claim 1, wherein the biosensor is a fully or partially implantable biosensor for continuously monitoring the analyte.

10. The method according to claim 1, wherein the analyte comprises glucose and the analyte value is determined by using glucose oxidase or glucose dehydrogenase as the enzyme.

11. An electronics unit for detecting in-vivo properties of a biosensor by performing a method according to claim 1.

12. The electronics unit according to claim 11, wherein the electronics unit is further adapted for:
   applying an electrical potential between the working electrode and a reference electrode of the biosensor; and
   measuring the raw current generated thereby, wherein the electronics unit comprises a direct current measuring unit configured for measuring the raw current.

13. A system for operating a biosensor for electrochemically detecting an analyte value in a sample of a body fluid, the system comprising a biosensor operable by performing a method according to claim 1.

* * * * *